(12) United States Patent
French et al.

(10) Patent No.: US 6,821,767 B1
(45) Date of Patent: Nov. 23, 2004

(54) ANDROGEN RECEPTOR PROTEINS, RECOMBINANT DNA MOLECULES CODING FOR SUCH, AND USE OF SUCH COMPOSITIONS

(75) Inventors: Frank S. French, Chapel Hill, NC (US); Elizabeth M. Wilson, Chapel Hill, NC (US); David R. Joseph, Chapel Hill, NC (US); Dennis Bryant Lubahn, Columbia, MO (US)

(73) Assignee: The University of North Carolina at Chapel Hill, Chapel Hill, NC (US)

( * ) Notice: Subject to any disclaimer, the term of this patent is extended or adjusted under 35 U.S.C. 154(b) by 0 days.

(21) Appl. No.: 09/497,822

(22) Filed: Feb. 3, 2000

Related U.S. Application Data

(62) Division of application No. 07/182,646, filed on Apr. 15, 1988.

(51) Int. Cl.[7] ............................ C12N 15/12; C12N 5/10
(52) U.S. Cl. ............................... 435/232.3; 435/320.1; 435/325; 536/23.5
(58) Field of Search ...................... 536/23.5; 435/320.1, 435/325, 252.33, 172.3

(56) References Cited

U.S. PATENT DOCUMENTS

| | | |
|---|---|---|
| 4,423,208 A | 12/1983 | Grandics |
| 5,614,620 A | 3/1997 | Liao et al. |

FOREIGN PATENT DOCUMENTS

| | | |
|---|---|---|
| EP | 0 365 657 B1 | 8/1999 |
| WO | WO 87/05049 | 8/1987 |
| WO | WO 89/09223 | 10/1989 |
| WO | WO 89/09791 A1 | 10/1989 |

OTHER PUBLICATIONS

Arriza et al.; *Cloning of Human Mineralocorticoid Receptor Complementary DNA: Structural and Functional Kinship with the Gluocorticoid Receptor*, Science 237:268 (1987).
Barrack et al.; *A Critical Evaluation of the Use of Androgen Receptor Assays to Predict the Androgen Responsiveness of Prostatic Cancer*, Progress in Clinical and Biological Research, Coffey et al., Editors, 239:155 (1987).
Chang et al., *Molecular Cloning of Human and Rat Complementary DNA Encoding Androgen Receptors*, Science, 240:324–326 (1988).
Chang et al., *Structural analysis of complementary DNA and amino acid sequences of human and rat androgen receptors*, Proceedings of the National Academy of Sciences of the USA, 85:7211–7215 (1988).
Foekens et al., *Purification of the androgen receptor of sheep seminal vesicles*, Biochemical and Biophysical Research Communications, 104:1279–1286(1982).

Foekens, et al.; *Purification of the androgen receptor of sheep seminal vesicles*, Chemical Abstracts, 96:136059r; p. 106 (1982).
Govindan, *Cloning of the human androgen receptor of cDNA*, Chemical Absracts, 109(23), p. 205 (1988).
Green, *Human oestrogen receptor cDNA. sequence, expression and homology to v–erb–A*, Nature, 320:134–139 (1986).
Greene et al.; *Sequence and Expression of Human Estrogen Receptor Complementary DNA*, Science 231:1150 (1986).
Hollenberg et al.; *Primary Structure and Expression of a Functional Human Glucocorticoid Receptor cDNA*, Science 318:635 (1986).
Johnson et al.; *A Common Molecular Weight of the Androgen Receptor Monomer in Different Target Tissues*, Biochemistry 26:3174–3182 (Jun. 2, 1987).
Lubahn et al., *The human androgen receptor: complementary deoxyribonucleic acid cloning, sequence analysis and gene expression in prostate*, Molecular Endocrinology, 2:1265–1275 (1988).
Lubahn, *Cloning of Human Androgen Receoptor Complementary DNA and Localization to the X Chromosome*; Science, 240:327–330 (1988).
Misrahi et al.; *Complete Amino Acid Sequence of the Human Progesterone Receptor Deduced from Cloned cDNA*, Biophys. Res. Comm. 143:740 (1987).
Murthy et al.; *Physicochemical Characterization of the Androgen Receptor From Hyperplastic Human Prostate*, The Prostate 5:567–579 (1984).
Rowley et al.; *Properties of an Intermediate–Sized Androgen Receptor: Association with RNA*, Biochemistry 25:6988–6995 (1986).
Tilley et al., *Characterization and expression of a cDNA encoding the human androgen receptor*, Proceedings of the National Academy of Sciences of the USA, 86:327–331 (1989).
Trapman, *Cloning Structure and Expression of a cDNA Encoding the Human Androgen Receptor*, Biochemical and Biophysical Research Communications, 153:241–248 (1988).
Weinberger, *The c–erb–A gene encodes a thyroid hormone receptor*, Nature, 324:641–646 (1986).

*Primary Examiner*—Michael Pak
(74) *Attorney, Agent, or Firm*—Myers Bigel Sibley & Sajovec

(57) ABSTRACT

DNA sequences encoding human androgen receptor protein and polypeptides and proteins having substantially the same biological activity as human androgen receptor protein and the amino acid sequences of human androgen receptor protein and polypeptides and proteins having substantially the same biological activity as human androgen receptor protein are disclosed. Methods for the production and use of such compositions are also disclosed.

9 Claims, 23 Drawing Sheets

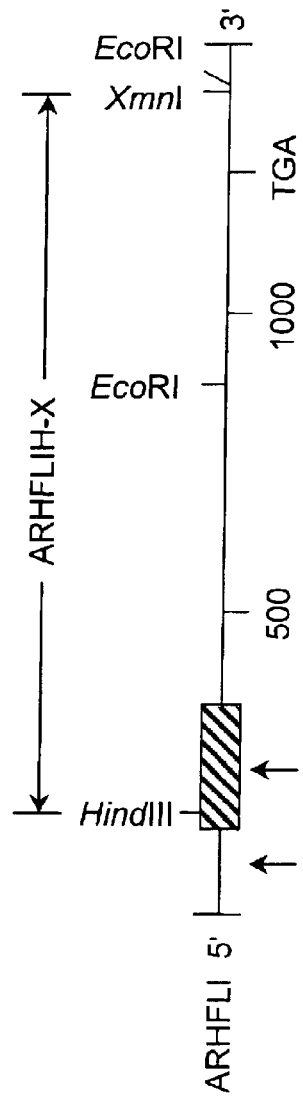

DNA-BINDING DOMAIN

```
                                    +            10            +         20+              30
hAR    (AA 567) (SEQ ID NO:9)     C L I C G D E A S G C H Y G A L T C G S C K V F F K R A A E G  (100%)
hPR    (AA 603) (SEQ ID NO:10)    C L I C G D E A S G C H Y G V L T C G S C K V F F K R A M E G  (94%)
hMR    (AA 421) (SEQ ID NO:11)    C L V C S D E A S G C H Y G V V T C G S C K V F F K R A V E G  (87%)
hGR    (AA 185) (SEQ ID NO:12)    C L V C S D E A S G C H Y G V L T C G S C K V F F K R A V E G  (87%)
hER             (SEQ ID NO:13)    C A V C N D Y A S G Y H Y G V W S C E G C K A F F K R S I Q G  (55%)
cVDR            (SEQ ID NO:14)    C G V C G D R A T G F H F N A M T C E G C K G F F R R S M K R  (48%)
hT3R   (AA 102) (SEQ ID NO:15)    C V V C G D K A T G Y H Y R C I T C E G C K G F F R R T I Q K  (48%)
vERBA  (AA 37)  (SEQ ID NO:16)    C V V C G D K A T G Y H Y R C I T C E G C K G F F R R T I Q K  (48%)
hRAR   (AA 58)  (SEQ ID NO:17)    C F V C Q D K S S G Y H Y G V S A C E G C K G F F R R S I Q K  (45%)

+         40          +               50         +      60+
hAR             (SEQ ID NO:9)         K Q K Y L C A S R N D C T I D K F R R K N C P S C R L R K C Y E A G M  (100%)
hPR             (SEQ ID NO:10)        Q H N Y L C A G R N D C I V D K I R R K N C P A C R L R K C C Q A G M  (71%)
hMR             (SEQ ID NO:11)        Q H N Y L C A G R N D C I I D K I R R K N C P A C R L Q K C L Q A G M  (71%)
hGR             (SEQ ID NO:12)        Q H N Y L C A G R N D C I I D K I R R K N C P A C R Y R K C L Q A G M  (71%)
hER             (SEQ ID NO:13)        H N D Y M C P A T N Q C T I D K N R R K S C Q A C R L R K C Y E V G M  (63%)
cVDR            (SEQ ID NO:14)        K A M F T C P F N G D C K I T K D N R R H C Q A C R L K R C V D I G M  (40%)
hT3R        N L (SEQ ID NO:15)        H P S Y S C K Y E G K C V I D K V T R N Q C Q L C R F K K C I Y V G M  (40%)
vERBA       N L (SEQ ID NO:16)        H P T T S C T Y D G K C V I H K V T R N Q C Q Y C R L Q K C F E V G M  (37%)
hRAR            (SEQ ID NO:17)        N M V Y T C H R D K N C I I N K V T R N R C Q Y C R L Q K C F E V G M  (43%)
```

FIG. 1C

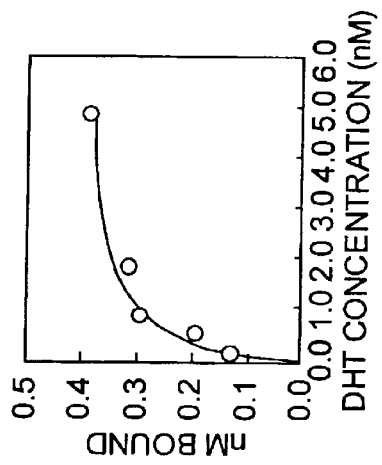
*FIG. 2A*
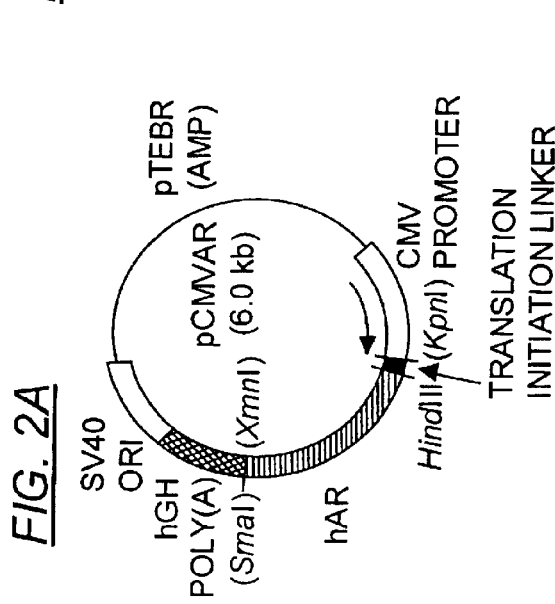
*FIG. 2B*
*FIG. 2C*
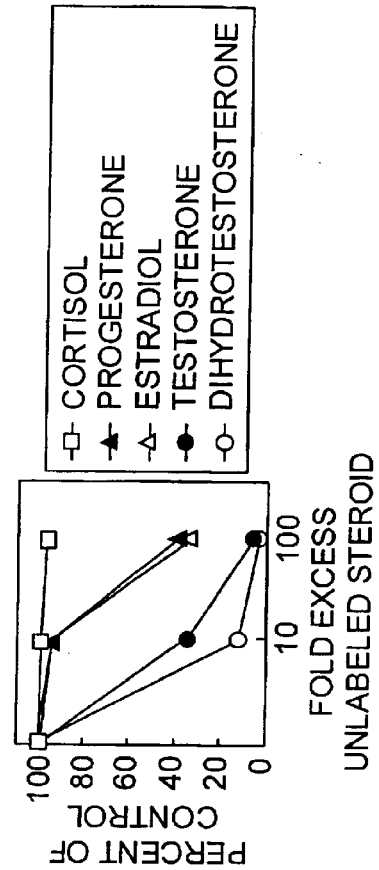
*FIG. 2D*

```
            10                      30                      50
             .                       .                       .
GAGCTCTGGACAAAATTGAGCGCCTATGTGTACATGGCAAGTGTTTTAGTGTTTGTGTG
CTCGAGACCTGTTTTAACTCGCGGATACACATGTACCGTTCACAAAAATCACAAACACAC 70                      90                     110
             .                       .                       .
TTTACCTGCTTGTCTGGGTGATTTTGCCTTTGAGAGTCTGGATGAGAAATGCATGGTTAA
AAATGGACGAACAGACCCACTAAAACGGAAACTCTCAGACCTACTCTTTACGTACCAATT 130                     150                     170
             .                       .                       .
AGGCAATTCCAGACAGGAAGAAAGGCAGAGAAGAGGGTAGAAATGACCTCTGATTCTTGG
TCCGTTAAGGTCTGTCCTTCTTTCCGTCTCTTCTCCCATCTTTACTGGAGACTAAGAACC 190                     210                     230
             .                       .                       .
GGCTGAGGGTTCCTAGAGCAAATGGCACAATGCCACGAGGCCCGATCTATCCCTATGACG
CCGACTCCCAAGGATCTCGTTTACCGTGTTACGGTGCTCCGGGCTAGATAGGGATACTGC 250                     270                     290
             .                       .                       .
GAACTCTAAGGTTTCAGCATCAGCTATCTGCTGGCTTGGTCACTGGCTTGCCTCCTCAGT
CTTGAGATTCCAAAGTCGTAGTCGATAGACGACCGAACCAGTGACCGAACGGAGGAGTCA 310                     330                     350
             .                       .                       .
TTGTAGGAGACTCTCCCACTCTCCCATCTGCGCGCTCTTATCAGTCCTGAAAAGAACCCN
AACATCCTCTGAGAGGGTGAGAGGGTAGACGCGCGAGAATAGTCAGGACTTTTCTTGGGN 370                     390                     410
             .                       .                       .
TGGCNAGCCAGGAGCNAGGTATTCNTATCGTCCTTTTCNTCCTCCTNGCCTCACCTNGTT
ACCGNTCGGTCCTCGNTCCATAAGNATAGCAGGAAAAGNAGGAGGANCGGAGTGGANCAA 430                     450                     470
             .                       .                       .
GNTTTTTAGATTGGNCTTNGNAACCAAATTGTATGCTGGCCTCCAGGAAATCTGGAGCC
CNAAAAATCTAACCNGAANCNTTGGTTTAAACATACGACCGGAGGTCCTTTAGACCTCGG 490                     510                     530
             .                       .                       .
TGGCGCCTAAACCTTGGTTTAGGAAAGCAGGAGCTATTCAGGAAGCAGGGTCCTCCAGGG
ACCGCGGATTTGGAACCAAATCCTTTCGTCCTCGATAAGTCCTTCGTCCCAGGAGGTCCC 550                     570                     590
             .                       .                       .
CTAGAGCTAGCCTCTCCTGCCCTCGCCCACGTGCGCCAGCACTTGTTTCTCCAAAGCNAC
GATCTCGATCGGAGAGGACGGGAGCGGGTGCACGCGGTCGTGAACAAAGAGGTTTCGNTG
```

*FIG. 4A*

```
          610                 630                 650
           .                   .                   .
TAGGCAGGCGTTAGCGCGCGGTGAGGGGAGGGGAGAAAAGGAAAGGGGAGGGGAGGGAAA
ATCCGTCCGCAATCGCGCGCCACTCCCCTCCCCTCTTTTCCTTTCCCCTCCCCTCCCTTT 670                 690                 710
           .                   .                   .
AGGAGGTGGGAAGGCAAGGAGGCCGGCCNGGTGGGGGCGGGACCCGACTCGCANNAACTG
TCCTCCACCCTTCCGTTCCTCCGGCCGGNCCACCCCCGCCCTGGGCTGAGCGTNNTTGAC 730                 750                 770
           .                   .                   .
TTGCATTTGCTCTCCACCTCCCAGCGCCCCCTCCGAGATCCCGGGGAGCCAGCTTGCTGG
AACGTAAACGAGAGGTGGAGGGTCGCGGGGAGGCTCTAGGGCCCCTCGGTCGAACGACC 790                 810                 830
           .                   .                   .
GAGAGCGGGAACGGTCCGGAGCAAGCCCAGAGGCAGAGGAGGCGACAGAGGGAAAAAGGG
CTCTCGCCCTTGCCAGGCCTCGTTCGGGTCTCCGTCTCCTCCGCTGTCTCCCTTTTTCCC 850                 870                 890
           .                   .                   .
CCCNAGCTAGCCGCTCCAGTGCTGTACAGNAGCCGAAGGACGCACCACGCCAGCCCCAGC
GGGNTCGATCGGCGAGGTCACGACATGTCNTCGGCTTCCTGCGTGGTGCGGTCGGGGTCG 910                 930                 950
           .                   .                   .
CCGGCTCCAGCGACAGCNAACGCCTCTTGCANGCGTTCGAAGCCGCCGCCCGGAGCTGCC
GGCCGAGGTCGCTGTCGNTTGCGGAGAACGTNCGCAAGCTTCGGCGGCGGGCCTCGACGG 970                 990                1010
           .                   .                   .
CTTTCCTCTTCGGTGAAGTTTTTAAAAGCTGCTAAAGACTCGGAGGAAGCAAGGAAAGTG
GAAAGGAGAAGCCACTTCAAAAATTTTCGACGATTTCTGAGCCTCCTTCGTTCCTTTCAC 1030                1050                1070
           .                   .                   .
CCTGGTAGGACTGACGGCTGCCTTTGTCCTCCTCCTCTCCACCCCGCCTCCCCCCACCCT
GGACCATCCTGACTGCCGACGGAAACAGGAGGAGGAGAGGTGGGGCGGAGGGGGGTGGGA 1090                1110                1130
           .                   .                   .
GCCTTCCCCCCCTCCCCCGTCTTCTCTCCCGCAGCTGCCTCAGTCGGCTACTCTCAGCCA
CGGAAGGGGGGAGGGGGCAGAAGAGAGGGCGTCGACGGAGTCAGCCGATGAGAGTCGGT 1150                1170                1190
           .                   .                   .
ACCCCCCTCACCACCCTTCTCCCCACCCGCCCCCCGCCCCCGTCGGCCCAGCGNTGNCA
TGGGGGGAGTGGTGGGAAGAGGGGTGGGCGGGGGGGCGGGGGCAGCCGGGTCGCNACNGT
```

*FIG. 4B*

```
         1210                1230                1250
          .                   .                   .
GNCCGAGTTTGCAGAGAGGTAACTCCCTTTGGCTGCGAGCGGGCGAGNCTAGCTGCACAT
CNGGCTCAAACGTCTCTCCATTGAGGGAAACCGACGCTCGCCCGCTCNGATCGACGTGTA 1270                1290                1310
          .                   .                   .
TGCAAAGAAGGCTCTTAGGAGCAGGCGACTGGGGAGCGGCTTCAGCACTGCAGCCACGAC
ACGTTTCTTCCGAGAATCCTCGTCCGCTGACCCCTCGCCGAAGTCGTGACGTCGGTGCTG 1330                1350                1370
          .                   .                   .
CNGCCTGGTTAGGCTGCACGCGGAGAGAACCCTCTGTTTTCCCCCACTCTCTCTCCACCT
GNCGGACCAATCCGACGTGCGCCTCTCTTGGGAGACAAAAGGGGGTGAGAGAGAGGTGGA 1390                1410                1430
          .                   .                   .
CCTCCTGCCTTCCCCACCCCGAGTGCGGAGCCAGAGATCAAAAGATGAAAAGGCAGTCAG
GGAGGACGGAAGGGGTGGGGCTCACGCCTCGGTCTCTAGTTTTCTACTTTTCCGTCAGTC 1450                1470                1490
          .                   .                   .
GTCTTCAGTAGCCAAAAAACAAAACAAACAAAAACAAAAAAGCCGAAATAAAAGAAAAAG
CAGAAGTCATCGGTTTTTTGTTTTGTTTGTTTTGTTTTTTCGGCTTTATTTTCTTTTTC 1510                1530                1550
          .                   .                   .
ATAATAACTCAGTTCTTATTTGCACCTACTTCAGTGGACACTGAATTTGGAAGGTGGAGG
TATTATTGAGTCAAGAATAAACGTGGATGAAGTCACCTGTGACTTAAACCTTCCACCTCC 1570                1590                1610
          .                   .                   .
ATTTTGTTTTTTTCTTTTAAGATCTGGGCATCTTTTGAATCTACCCTTCAAGTATTAAGA
TAAAACAAAAAAAGAAAATTCTAGACCCGTAGAAAACTTAGATGGGAAGTTCATAATTCT 1630                1650                1670
          .                   .                   .
GACAGACTGTGAGCCTAGCAGGGCAGATCTTGTCCACCGTGTGTCTTCTTCTGCACGAGA
CTGTCTGACACTCGGATCGTCCCGTCTAGAACAGGTGGCACACAGAAGAAGACGTGCTCT 1690                1710                1730
          .                   .                   .
CTTTGAGGCTGTCAGAGCGCTTTTTGCGTGGTTGCTCCCGCAAGTTTCCTTCTCTGGAGC
GAAACTCCGACAGTCTCGCGAAAAACGCACCAACGAGGGCGTTCAAAGGAAGAGACCTCG 1750                1770                1790
          .                   .                   .
TTCCCGCAGGTGGGCAGCTAGCTGCAGCGACTACCGCATCATCACAGCCTGTTGAACTCT
AAGGGCGTCCACCCGTCGATCGACGTCGCTGATGGCGTAGTAGTGTCGGACAACTTGAGA
```

FIG. 4C

```
              1810                  1830                  1850
               .                     .                     .
TCTGAGCAAGAGAAGGGGAGGCGGGGTAAGGGAAGTAGGTGGAAGATTCAGCCAAGCTCA
AGACTCGTTCTCTTCCCCTCCGCCCCATTCCCTTCATCCACCTTCTAAGTCGGTTCGAGT 1870                  1890                  1910
               .                     .                     .
AGGATGGAAGTGCAGTTAGGGCTGGGAAGGGTCTACCCTCGGCCGCCGTCCAAGACCTAC
TCCTACCTTCACGTCAATCCCGACCCTTCCCAGATGGGAGCCGGCGGCAGGTTCTGGATG 1930                  1950                  1970
               .                     .                     .
CGAGGAGCTTTCCAGAATCTGTTCCAGAGCGTGCGCGAAGTGATCCAGAACCCGGGCCCC
GCTCCTCGAAAGGTCTTAGACAAGGTCTCGCACGCGCTTCACTAGGTCTTGGGCCCGGGG 1990                  2010                  2030
               .                     .                     .
AGGCACCCAGAGGCCGCGAGCGCAGCACCTCCCGGCGCCAGTTTGCTGCTGCTGCAGCAG
TCCGTGGGTCTCCGGCGCTCGCGTCGTGGAGGGCCGCGGTCAAACGACGACGACGTCGTC 2050                  2070                  2090
               .                     .                     .
CAGCAGCAGCAGCAGCAGCAGCAGCAGCAGCAGCAGCAGCAGCAGCAGCAGCAGCAGCAG
GTCGTCGTCGTCGTCGTCGTCGTCGTCGTCGTCGTCGTCGTCGTCGTCGTCGTCGTCGTC 2110                  2130                  2150
               .                     .                     .
CAGCAGCAAGAGACTAGCCCCAGGCAGCAGCAGCAGCAGCAGGGTGAGGATGGTTCTCCC
GTCGTCGTTCTCTGATCGGGGTCCGTCGTCGTCGTCGTCGTCCCACTCCTACCAAGAGGG 2170                  2190                  2210
               .                     .                     .
CAAGCCCATCGTAGAGGCCCCACAGGCTACCTGGTCCTGGATGAGGAACAGCAACCTTCA
GTTCGGGTAGCATCTCCGGGGTGTCCGATGGACCAGGACCTACTCCTTGTCGTTGGAAGT 2230                  2250                  2270
               .                     .                     .
CAGCCGCAGTCGGCCCTGGAGTGCCACCCCGAGAGAGGTTGCGTCCCAGAGCCTGGAGCC
GTCGGCGTCAGCCGGGACCTCACGGTGGGGCTCTCTCCAACGCAGGGTCTCGGACCTCGG 2290                  2310                  2330
               .                     .                     .
GCCGTGGCCGCCAGCAAGGGGCTGCCGCAGCAGCTGCCAGCACCTCCGGACGAGGATGAC
CGGCACCGGCGGTCGTTCCCCGACGGCGTCGTCGACGGTCGTGGAGGCCTGCTCCTACTG 2350                  2370                  2390
               .                     .                     .
TCAGCTGCCCCATCCACGTTGTCCCTGCTGGGCCCCACTTTCCCCGGCTTAAGCAGCTGC
AGTCGACGGGGTAGGTGCAACAGGGACGACCCGGGGTGAAAGGGGCCGAATTCGTCGACG
```

*FIG. 4D*

```
                2410                    2430                    2450
                 .                       .                       .
         TCCGCTGACCTTAAAGACATCCTGAGCGAGGCCAGCACCATGCAACTCCTTCAGCAACAG
         AGGCGACTGGAATTTCTGTAGGACTCGCTCCGGTCGTGGTACGTTGAGGAAGTCGTTGTC 2470                    2490                    2510
                 .                       .                       .
         CAGCAGGAAGCAGTATCCGAAGGCAGCAGCAGCGGGAGAGCGAGGGAGGCCTCGGGGGCT
         GTCGTCCTTCGTCATAGGCTTCCGTCGTCGTCGCCCTCTCGCTCCCTCCGGAGCCCCCGA 2530                    2550                    2570
                 .                       .                       .
         CCCACTTCCTCCAAGGACAATTACTTAGGGGGCACTTCGACCATTTCTGACAACGCCAAG
         GGGTGAAGGAGGTTCCTGTTAATGAATCCCCCGTGAAGCTGGTAAAGACTGTTGCGGTTC 2590                    2610                    2630
                 .                       .                       .
         GAGTTGTGTAAGGCAGTGTCGGTGTCCATGGGCCTGGGTGTGGAGGCGTTGGAGCATCTG
         CTCAACACATTCCGTCACAGCCACAGGTACCCGGACCCACACCTCCGCAACCTCGTAGAC 2650                    2670                    2690
                 .                       .                       .
         AGTCCAGGGGAACAGCTTCGGGGGGATTGCATGTACGCCCCACTTTTGGGAGTTCCACCC
         TCAGGTCCCCTTGTCGAAGCCCCCCTAACGTACATGCGGGGTGAAAACCCTCAAGGTGGG 2710                    2730                    2750
                 .                       .                       .
         GCTGTGCGTCCCACTCCTTGTGCCCCATTGGCCGAATGCAAAGGTTCTCTGCTAGACGAC
         CGACACGCAGGGTGAGGAACACGGGGTAACCGGCTTACGTTTCCAAGAGACGATCTGCTG 2770                    2790                    2810
                 .                       .                       .
         AGCGCAGGCAAGAGCACTGAAGATACTGCTGAGTATTCCCCTTTCAAGGGAGGTTACACC
         TCGCGTCCGTTCTCGTGACTTCTATGACGACTCATAAGGGGAAAGTTCCCTCCAATGTGG 2830                    2850                    2870
                 .                       .                       .
         AAAGGGCTAGAAGGCGAGAGCCTAGGCTGCTCTGGCAGCGCTGCAGCAGGGAGCTCCGGG
         TTTCCCGATCTTCCGCTCTCGGATCCGACGAGACCGTCGCGACGTCGTCCCTCGAGGCCC 2890                    2910                    2930
                 .                       .                       .
         ACACTTGAACTGCCGTCTACCCTGTCTCTCTACAAGTCCGGAGCACTGGACGAGGCAGCT
         TGTGAACTTGACGGCAGATGGGACAGAGAGATGTTCAGGCCTCGTGACCTGCTCCGTCGA 2950                    2970                    2990
                 .                       .                       .
         GCGTACCAGAGTCGCGACTACTACAACTTTCCACTGGCTCTGGCCGGACCGCCGCCCCCT
         CGCATGGTCTCAGCGCTGATGATGTTGAAAGGTGACCGAGACCGGCCTGGCGGCGGGGA
```

*FIG. 4E*

```
                3010                    3030                    3050
                   .                       .                       .
       CCGCCGCCTCCCCATCCCCACGCTCGCATCAAGCTGGAGAACCCGCTGGACTACGGCAGC
       GGCGGCGGAGGGGTAGGGGTGCGAGCGTAGTTCGACCTCTTGGGCGACCTGATGCCGTCG 3070                    3090                    3110
                   .                       .                       .
       GCCTGGGCGGCTGCGGCGGCGCAGTGCCGCTATGGGGACCTGGCGAGCCTGCATGGCGCG
       CGGACCCGCCGACGCCGCCGCGTCACGGCGATACCCCTGGACCGCTCGGACGTACCGCGC 3130                    3150                    3170
                   .                       .                       .
       GGTGCAGCGGGACCCGGTTCTGGGTCACCCTCAGCCGCCGCTTCCTCATCCTGGCACACT
       CCACGTCGCCCTGGGCCAAGACCCAGTGGGAGTCGGCGGCGAAGGAGTAGGACCGTGTGA 3190                    3210                    3230
                   .                       .                       .
       CTCTTCACAGCCGAAGAAGGCCAGTTGTATGGACCGTGTGGTGGTGGTGGGGGTGGTGGC
       GAGAAGTGTCGGCTTCTTCCGGTCAACATACCTGGCACACCACCACCACCCCCACCACCG 3250                    3270                    3290
                   .                       .                       .
       GGCGGCGGCGGCGGCGGCGGCGGCGGCGGCGGCGGCGGCGGCGGCGGCGGCGAGGCGGGA
       CCGCCGCCGCCGCCGCCGCCGCCGCCGCCGCCGCCGCCGCCGCCGCCGCCGCTCCGCCCT 3310                    3330                    3350
                   .                       .                       .
       GCTGTAGCCCCCTACGGCTACACTCGGCCCCCTCAGGGGCTGGCGGGCCAGGAAAGCGAC
       CGACATCGGGGGATGCCGATGTGAGCCGGGGGAGTCCCCGACCGCCCGGTCCTTTCGCTG 3370                    3390                    3410
                   .                       .                       .
       TTCACCGCACCTGATGTGTGGTACCCTGGCGGCATGGTGAGCAGAGTGCCCTATCCCAGT
       AAGTGGCGTGGACTACACACCATGGGACCGCCGTACCACTCGTCTCACGGGATAGGGTCA 3430                    3450                    3470
                   .                       .                       .
       CCCACTTGTGTCAAAAGCGAAATGGGCCCCTGGATGGATAGCTACTCCGGACCTTACGGG
       GGGTGAACACAGTTTTCGCTTTACCCGGGGACCTACCTATCGATGAGGCCTGGAATGCCC 3490                    3510                    3530
                   .                       .                       .
       GACATGCGTTTGGAGACTGCCAGGGACCATGTTTTGCCCATTGACTATTACTTTCCACCC
       CTGTACGCAAACCTCTGACGGTCCCTGGTACAAAACGGGTAACTGATAATGAAAGGTGGG 3550                    3570                    3590
                   .                       .                       .
       CAGAAGACCTGCCTGATCTGTGGAGATGAAGCTTCTGGGTGTCACTATGGAGCTCTCACA
       GTCTTCTGGACGGACTAGACACCTCTACTTCGAAGACCCACAGTGATACCTCGAGAGTGT
```

*FIG. 4F*

```
                3610                      3630                      3650
                  .                         .                         .
      TGTGGAAGCTGCAAGGTCTTCTTCAAAAGAGCCGCTGAAGGGAAACAGAAGTACCTGTGC
      ACACCTTCGACGTTCCAGAAGAAGTTTTCTCGGCGACTTCCCTTTGTCTTCATGGACACG 3670                      3690                      3710
                  .                         .                         .
      GCCAGCAGAAATGATTGCACTATTGATAAATTCCGAAGGAAAAATTGTCCATCTTGTCGT
      CGGTCGTCTTTACTAACGTGATAACTATTTAAGGCTTCCTTTTTAACAGGTAGAACAGCA 3730                      3750                      3770
                  .                         .                         .
      CTTCGGAAATGTTATGAAGCAGGGATGACTCTGGGAGCCCGGAAGCTGAAGAAACTTGGT
      GAAGCCTTTACAATACTTCGTCCCTACTGAGACCCTCGGGCCTTCGACTTCTTTGAACCA 3790                      3810                      3830
                  .                         .                         .
      AATCTGAAACTACAGGAGGAAGGAGAGGCTTCCAGCACCACCAGCCCCACTGAGGAGACA
      TTAGACTTTGATGTCCTCCTTCCTCTCCGAAGGTCGTGGTGGTCGGGGTGACTCCTCTGT 3850                      3870                      3890
                  .                         .                         .
      ACCCAGAAGCTGACAGTGTCACACATTGAAGGCTATGAATGTCAGCCCATCTTTCTGAAT
      TGGGTCTTCGACTGTCACAGTGTGTAACTTCCGATACTTACAGTCGGGTAGAAAGACTTA 3910                      3930                      3950
                  .                         .                         .
      GTCCTGGAAGCCATTGAGCCAGGTGTAGTGTGTGCTGGACACGACAACAACCAGCCCGAC
      CAGGACCTTCGGTAACTCGGTCCACATCACACACGACCTGTGCTGTTGTTGGTCGGGCTG 3970                      3990                      4010
                  .                         .                         .
      TCCTTTGCAGCCTTGCTCTCTAGCCTCAATGAACTGGGAGAGAGACAGCTTGTACACGTG
      AGGAAACGTCGGAACGAGAGATCGGAGTTACTTGACCCTCTCTCTGTCGAACATGTGCAC 4030                      4050                      4070
                  .                         .                         .
      GTCAAGTGGGCCAAGGCCTTGCCTGGCTTCCGCAACTTACACGTGGACGACCAGATGGCT
      CAGTTCACCCGGTTCCGGAACGGACCGAAGGCGTTGAATGTGCACCTGCTGGTCTACCGA 4090                      4110                      4130
                  .                         .                         .
      GTCATTCAGTACTCCTGGATGGGGCTCATGGTGTTTGCCATGGGCTGGCGATCCTTCACC
      CAGTAAGTCATGAGGACCTACCCCGAGTACCACAAACGGTACCCGACCGCTAGGAAGTGG 4150                      4170                      4190
                  .                         .                         .
      AATGTCAACTCCAGGATGCTCTACTTCGCCCCTGATCTGGTTTTCAATGAGTACCGCATG
      TTACAGTTGAGGTCCTACGAGATGAAGCGGGGACTAGACCAAAAGTTACTCATGGCGTAC
```

*FIG. 4G*

```
            4210                      4230                      4250
             .                         .                         .
CACAAGTCCCGGATGTACAGCCAGTGTGTCCGAATGAGGCACCTCTCTCAAGAGTTTGGA
GTGTTCAGGGCCTACATGTCGGTCACACAGGCTTACTCCGTGGAGAGAGTTCTCAAACCT 4270                      4290                      4310
             .                         .                         .
TGGCTCCAAATCACCCCCCAGGAATTCCTGTGCATGAAAGCACTGCTACTCTTCAGCATT
ACCGAGGTTTAGTGGGGGGTCCTTAAGGACACGTACTTTCGTGACGATGAGAAGTCGTAA 4330                      4350                      4370
             .                         .                         .
ATTCCAGTGGATGGGCTGAAAAATCAAAAATTCTTTGATGAACTTCGAATGAACTACATC
TAAGGTCACCTACCCGACTTTTTAGTTTTTAAGAAACTACTTGAAGCTTACTTGATGTAG 4390                      4410                      4430
             .                         .                         .
AAGGAACTCGATCGTATCATTGCATGCAAAAGAAAAAATCCCACATCCTGCTCAAGACGC
TTCCTTGAGCTAGCATAGTAACGTACGTTTTCTTTTTAGGGTGTAGGACGAGTTCTGCG 4450                      4470                      4490
             .                         .                         .
TTCTACCAGCTCACCAAGCTCCTGGACTCCGTGCAGCCTATTGCGAGAGAGCTGCATCAG
AAGATGGTCGAGTGGTTCGAGGACCTGAGGCACGTCGGATAACGCTCTCTCGACGTAGTC 4510                      4530                      4550
             .                         .                         .
TTCACTTTTGACCTGCTAATCAAGTCACACATGGTGAGCGTGGACTTTCCGGAAATGATG
AAGTGAAAACTGGACGATTAGTTCAGTGTGTACCACTCGCACCTGAAAGGCCTTTACTAC 4570                      4590                      4610
             .                         .                         .
GCAGAGATCATCTCTGTGCAAGTGCCCAAGATCCTTTCTGGGAAAGTCAAGCCCATCTAT
CGTCTCTAGTAGAGACACGTTCACGGGTTCTAGGAAAGACCCTTTCAGTTCGGGTAGATA 4630                      4650                      4670
             .                         .                         .
TTCCACACCCAGTGAAGCATTGGAAACCCTATTTCCCCACCCCAGCTCATGCCCCCTTTC
AAGGTGTGGGTCACTTCGTAACCTTTGGGATAAAGGGGTGGGGTCGAGTACGGGGGAAAG 4690                      4710                      4730
             .                         .                         .
AGATGTCTTCTGCCTGTTATAACTCTGCACTACTCCTCTGCAGTGCCTTGGGGAATTTCC
TCTACAGAAGACGGACAATATTGAGACGTGATGAGGAGACGTCACGGAACCCCTTAAAGG 4750                      4770                      4790
             .                         .                         .
TCTATTGATGTACAGTCTGTCATGAACATGTTCCTGAATTCTATTTGCTGGGCTTTTTTT
AGATAACTACATGTCAGACAGTACTTGTACAAGGACTTAAGATAAACGACCCGAAAAAAA
```

*FIG. 4H*

```
              4810                4830                4850
                .                   .                   .
               .         .         .         .         .
TTCTCTTTCTCTCCTTTCTTTTTCTTCTTCCCTCCCTATCTAACCCTCCCATGGCACCTT
AAGAGAAAGAGAGGAAAGAAAAAGAAGAAGGGAGGGATAGATTGGGAGGGTACCGTGGAA 4870                4890                4910
                .                   .                   .
               .         .         .         .         .
CAGACTTTGCTTCCCATTGTGGCTCCTATCTGTGTTTTGAATGGTGTTGTATGCCTTTAA
GTCTGAAACGAAGGGTAACACCGAGGATAGACACAAAACTTACCACAACATACGGAAATT 4930                4950                4970
                .                   .                   .
               .         .         .         .         .
ATCTGTGATGATCCTCATATGGCCCAGTGTCAAGTTGTGCTTGTTTACAGCACTACTCTG
TAGACACTACTAGGAGTATACCGGGTCACAGTTCAACACGAACAAATGTCGTGATGAGAC 4990                5010                5030
                .                   .                   .
               .         .         .         .         .
TGCCAGCCACACAAACGTTTACTTATCTTATGCCACGGGAAGTTTAGAGAGCTAAGATTA
ACGGTCGGTGTGTTTGCAAATGAATAGAATACGGTGCCCTTCAAATCTCTCGATTCTAAT 5050                5070
                .                   .
               .         .         .         .
TCTGGGGAAATCAAAACAAAAAACAAGCAAACAAAAAAAAAA
AGACCCCTTTAGTTTTGTTTTTTGTTCGTTTGTTTTTTTTTT
```

*FIG. 41*

```
   1 GAGCTCTGGACAAAATTGAGCGCCTATGTGTACATGGCAAGTGTTTTAGTGTTTGTGTG
  61 TTTACCTGCTTGTCTGGGTGATTTTGCCTTTGAGAGTCTGGATGAGAAATGCATGGTTAA
 121 AGGCAATTCCAGACAGGAAGAAAGGCAGAGAAGAGGGTAGAAATGACCTCTGATTCTTGG
 181 GGCTGAGGGTTCCTAGAGCAAATGGCACAATGCCACGAGGCCCGATCTATCCCTATGACG
 241 GAACTCTAAGGTTTCAGCATCAGCTATCTGCTGGCTTGGTCACTGGCTTGCCTCCTCAGT
 301 TTGTAGGAGACTCTCCCACTCTCCCATCTGCGCGCTCTTATCAGTCCTGAAAAGAACCCN
 361 TGGCNAGCCAGGAGCNAGGTATTCNTATCGTCCTTTTCNTCCTCCTNGCCTCACCTNGTT
 421 GNTTTTTAGATTGGNCTTNGNAACCAAATTTGTATGCTGGCCTCCAGGAAATCTGGAGCC
 481 TGGCGCCTAAACCTTGGTTTAGGAAAGCAGGAGCTATTCAGGAAGCAGGGTCCTCCAGGG
 541 CTAGAGCTAGCCTCTCCTGCCCTCGCCCACGTGCGCCAGCACTTGTTTCTCCAAAGCNAC
 601 TAGGCAGGCGTTAGCGCGCGGTGAGGGGAGGGGAGAAAAGGAAAGGGGAGGGGAGGGAAA
 661 AGGAGGTGGGAAGGCAAGGAGGCCGGCCNGGTGGGGGCGGGACCCGACTCGCANNAACTG
 721 TTGCATTTGCTCTCCACCTCCCAGCGCCCCCTCCGAGATCCCGGGGAGCCAGCTTGCTGG
 781 GAGAGCGGGAACGGTCCGGAGCAAGCCCAGAGGCAGAGGAGGCGACAGAGGGAAAAGGG
 841 CCCNAGCTAGCCGCTCCAGTGCTGTACAGNAGCCGAAGGACGCACCACGCCAGCCCCAGC
 901 CCGGCTCCAGCGACAGCNAACGCCTCTTGCANGCGTTCGAAGCCGCCGCCCGGAGCTGCC
 961 CTTTCCTCTTCGGTGAAGTTTTTAAAAGCTGCTAAAGACTCGGAGGAAGCAAGGAAAGTG
1021 CCTGGTAGGACTGACGGCTGCCTTTGTCCTCCTCCTCTCCACCCCGCCTCCCCCCACCCT
1081 GCCTTCCCCCCCTCCCCCGTCTTCTCTCCCGCAGCTGCCTCAGTCGGCTACTCTCAGCCA
1141 ACCCCCCTCACCACCCTTCTCCCCACCCGCCCCCCCGCCCCCGTCGGCCCAGCGNTGNCA
1201 GNCCGAGTTTGCAGAGAGGTAACTCCCTTTGGCTGCGAGCGGGCGAGNCTAGCTGCACAT
1261 TGCAAAGAAGGCTCTTAGGAGCAGGCGACTGGGGAGCGGCTTCAGCACTGCAGCCACGAC
1321 CNGCCTGGTTAGGCTGCACGCGGAGAGAACCCTCTGTTTTCCCCCACTCTCTCTCCACCT
1381 CCTCCTGCCTTCCCCACCCCGAGTGCGGAGCCAGAGATCAAAAGATGAAAAGGCAGTCAG
1441 GTCTTCAGTAGCCAAAAAACAAAACAAACAAAAACAAAAAAGCCGAAATAAAAGAAAAAG
```

*FIG. 5A*

```
1501 ATAATAACTCAGTTCTTATTTGCACCTACTTCAGTGGACACTGAATTTGGAAGGTGGAGG

1561 ATTTTGTTTTTTCTTTTAAGATCTGGGCATCTTTTGAATCTACCCTTCAAGTATTAAGA

1621 GACAGACTGTGAGCCTAGCAGGGCAGATCTTGTCCACCGTGTGTCTTCTTCTGCACGAGA

1681 CTTTGAGGCTGTCAGAGCGCTTTTTGCGTGGTTGCTCCCGCAAGTTTCCTTCTCTGGAGC

1741 TTCCCGCAGGTGGGCAGCTAGCTGCAGCGACTACCGCATCATCACAGCCTGTTGAACTCT

1801 TCTGAGCAAGAGAAGGGGAGGCGGGGTAAGGGAAGTAGGTGGAAGATTCAGCCAAGCTCA

1861 AGGATGGAAGTGCAGTTAGGGCTGGGAAGGGTCTACCCTCGGCCGCCGTCCAAGACCTAC
      MetGluValGlnLeuGlyLeuGlyArgValTyrProArgProProSerLysThrTyr

1921 CGAGGAGCTTTCCAGAATCTGTTCCAGAGCGTGCGCGAAGTGATCCAGAACCCGGGCCCC
      ArgGlyAlaPheGlnAsnLeuPheGlnSerValArgGluValIleGlnAsnProGlyPro

1981 AGGCACCCAGAGGCCGCGAGCGCAGCACCTCCCGGCGCCAGTTTGCTGCTGCTGCAGCAG
      ArgHisProGluAlaAlaSerAlaAlaProProGlyAlaSerLeuLeuLeuLeuGlnGln

2041 CAGCAGCAGCAGCAGCAGCAGCAGCAGCAGCAGCAGCAGCAGCAGCAGCAGCAGCAGCAG
      GlnGlnGlnGlnGlnGlnGlnGlnGlnGlnGlnGlnGlnGlnGlnGlnGlnGlnGlnGln

2101 CAGCAGCAAGAGACTAGCCCCAGGCAGCAGCAGCAGCAGCAGGGTGAGGATGGTTCTCCC
      GlnGlnGlnGluThrSerProArgGlnGlnGlnGlnGlnGlnGlyGluAspGlySerPro

2161 CAAGCCCATCGTAGAGGCCCCACAGGCTACCTGGTCCTGGATGAGGAACAGCAACCTTCA
      GlnAlaHisArgArgGlyProThrGlyTyrLeuValLeuAspGluGluGlnGlnProSer

2221 CAGCCGCAGTCGGCCCTGGAGTGCCACCCCGAGAGAGGTTGCGTCCCAGAGCCTGGAGCC
      GlnProGlnSerAlaLeuGluCysHisProGluArgGlyCysValProGluProGlyAla

2281 GCCGTGGCCGCCAGCAAGGGGCTGCCGCAGCAGCTGCCAGCACCTCCGGACGAGGATGAC
      AlaValAlaAlaSerLysGlyLeuProGlnGlnLeuProAlaProProAspGluAspAsp

2341 TCAGCTGCCCCATCCACGTTGTCCCTGCTGGGCCCCACTTTCCCCGGCTTAAGCAGCTGC
      SerAlaAlaProSerThrLeuSerLeuLeuGlyProThrPheProGlyLeuSerSerCys

2401 TCCGCTGACCTTAAAGACATCCTGAGCGAGGCCAGCACCATGCAACTCCTTCAGCAACAG
      SerAlaAspLeuLysAspIleLeuSerGluAlaSerThrMetGlnLeuLeuGlnGlnGln

2461 CAGCAGGAAGCAGTATCCGAAGGCAGCAGCAGCGGGAGAGCGAGGGAGGCCTCGGGGGCT
      GlnGlnGluAlaValSerGluGlySerSerSerGlyArgAlaArgGluAlaSerGlyAla

2521 CCCACTTCCTCCAAGGACAATTACTTAGGGGGCACTTCGACCATTTCTGACAACGCCAAG
      ProThrSerSerLysAspAsnTyrLeuGlyGlyThrSerThrIleSerAspAsnAlaLys
```

*FIG. 5B*

2581 GAGTTGTGTAAGGCAGTGTCGGTGTCCATGGGCCTGGGTGTGGAGGCGTTGGAGCATCTG
     GluLeuCysLysAlaValSerValSerMetGlyLeuGlyValGluAlaLeuGluHisLeu

2641 AGTCCAGGGGAACAGCTTCGGGGGGATTGCATGTACGCCCCACTTTTGGGAGTTCCACCC
     SerProGlyGluGlnLeuArgGlyAspCysMetTyrAlaProLeuLeuGlyValProPro

2701 GCTGTGCGTCCCACTCCTTGTGCCCCATTGGCCGAATGCAAAGGTTCTCTGCTAGACGAC
     AlaValArgProThrProCysAlaProLeuAlaGluCysLysGlySerLeuLeuAspAsp

2761 AGCGCAGGCAAGAGCACTGAAGATACTGCTGAGTATTCCCCTTTCAAGGGAGGTTACACC
     SerAlaGlyLysSerThrGluAspThrAlaGluTyrSerProPheLysGlyGlyTyrThr

2821 AAAGGGCTAGAAGGCGAGAGCCTAGGCTGCTCTGGCAGCGCTGCAGCAGGGAGCTCCGGG
     LysGlyLeuGluGlyGluSerLeuGlyCysSerGlySerAlaAlaAlaGlySerSerGly

2881 ACACTTGAACTGCCGTCTACCCTGTCTCTCTACAAGTCCGGAGCACTGGACGAGGCAGCT
     ThrLeuGluLeuProSerThrLeuSerLeuTyrLysSerGlyAlaLeuAspGluAlaAla

2941 GCGTACCAGAGTCGCGACTACTACAACTTTCCACTGGCTCTGGCCGGACCGCCGCCCCCT
     AlaTyrGlnSerArgAspTyrTyrAsnPheProLeuAlaLeuAlaGlyProProProPro

3001 CCGCCGCCTCCCCATCCCCACGCTCGCATCAAGCTGGAGAACCCGCTGGACTACGGCAGC
     ProProProProHisProHisAlaArgIleLysLeuGluAsnProLeuAspTyrGlySer

3061 GCCTGGGCGGCTGCGGCGGCGCAGTGCCGCTATGGGGACCTGGCGAGCCTGCATGGCGCG
     AlaTrpAlaAlaAlaAlaAlaGlnCysArgTyrGlyAspLeuAlaSerLeuHisGlyAla

3121 GGTGCAGCGGGACCCGGTTCTGGGTCACCCTCAGCCGCCGCTTCCTCATCCTGGCACACT
     GlyAlaAlaGlyProGlySerGlySerProSerAlaAlaAlaSerSerSerTrpHisThr

3181 CTCTTCACAGCCGAAGAAGGCCAGTTGTATGGACCGTGTGGTGGTGGTGGGGGTGGTGGC
     LeuPheThrAlaGluGluGlyGlnLeuTyrGlyProCysGlyGlyGlyGlyGlyGlyGly

3241 GGCGGCGGCGGCGGCGGCGGCGGCGGCGGCGGCGGCGGCGGCGGCGAGGCGGGA
     GlyGlyGlyGlyGlyGlyGlyGlyGlyGlyGlyGlyGlyGlyGlyGlyGluAlaGly

3301 GCTGTAGCCCCCTACGGCTACACTCGGCCCCCTCAGGGGCTGGCGGGCCAGGAAAGCGAC
     AlaValAlaProTyrGlyTyrThrArgProProGlnGlyLeuAlaGlyGlnGluSerAsp

3361 TTCACCGCACCTGATGTGTGGTACCCTGGCGGCATGGTGAGCAGAGTGCCCTATCCCAGT
     PheThrAlaProAspValTrpTyrProGlyGlyMetValSerArgValProTyrProSer

3421 CCCACTTGTGTCAAAAGCGAAATGGGCCCCTGGATGGATAGCTACTCCGGACCTTACGGG
     ProThrCysValLysSerGluMetGlyProTrpMetAspSerTyrSerGlyProTyrGly

3481 GACATGCGTTTGGAGACTGCCAGGGACCATGTTTTGCCCATTGACTATTACTTTCCACCC
     AspMetArgLeuGluThrAlaArgAspHisValLeuProIleAspTyrTyrPheProPro

*FIG. 5C*

3541 CAGAAGACCTGCCTGATCTGTGGAGATGAAGCTTCTGGGTGTCACTATGGAGCTCTCACA
     GlnLysThrCysLeuIleCysGlyAspGluAlaSerGlyCysHisTyrGlyAlaLeuThr

3601 TGTGGAAGCTGCAAGGTCTTCTTCAAAAGAGCCGCTGAAGGGAAACAGAAGTACCTGTGC
     CysGlySerCysLysValPhePheLysArgAlaAlaGluGlyLysGlnLysTyrLeuCys

3661 GCCAGCAGAAATGATTGCACTATTGATAAATTCCGAAGGAAAAATTGTCCATCTTGTCGT
     AlaSerArgAsnAspCysThrIleAspLysPheArgArgLysAsnCysProSerCysArg

3721 CTTCGGAAATGTTATGAAGCAGGGATGACTCTGGGAGCCCGGAAGCTGAAGAAACTTGGT
     LeuArgLysCysTyrGluAlaGlyMetThrLeuGlyAlaArgLysLeuLysLysLeuGly

3781 AATCTGAAACTACAGGAGGAAGGAGAGGCTTCCAGCACCACCAGCCCCACTGAGGAGACA
     AsnLeuLysLeuGlnGluGluGlyGluAlaSerSerThrThrSerProThrGluGluThr

3841 ACCCAGAAGCTGACAGTGTCACACATTGAAGGCTATGAATGTCAGCCCATCTTTCTGAAT
     ThrGlnLysLeuThrValSerHisIleGluGlyTyrGluCysGlnProIlePheLeuAsn

3901 GTCCTGGAAGCCATTGAGCCAGGTGTAGTGTGTGCTGGACACGACAACAACCAGCCCGAC
     ValLeuGluAlaIleGluProGlyValValCysAlaGlyHisAspAsnAsnGlnProAsp

3961 TCCTTTGCAGCCTTGCTCTCTAGCCTCAATGAACTGGGAGAGAGACAGCTTGTACACGTG
     SerPheAlaAlaLeuLeuSerSerLeuAsnGluLeuGlyGluArgGlnLeuValHisVal

4021 GTCAAGTGGGCCAAGGCCTTGCCTGGCTTCCGCAACTTACACGTGGACGACCAGATGGCT
     ValLysTrpAlaLysAlaLeuProGlyPheArgAsnLeuHisValAspAspGlnMetAla

4081 GTCATTCAGTACTCCTGGATGGGGCTCATGGTGTTTGCCATGGGCTGGCGATCCTTCACC
     ValIleGlnTyrSerTrpMetGlyLeuMetValPheAlaMetGlyTrpArgSerPheThr

4141 AATGTCAACTCCAGGATGCTCTACTTCGCCCCTGATCTGGTTTTCAATGAGTACCGCATG
     AsnValAsnSerArgMetLeuTyrPheAlaProAspLeuValPheAsnGluTyrArgMet

4201 CACAAGTCCCGGATGTACAGCCAGTGTGTCCGAATGAGGCACCTCTCTCAAGAGTTTGGA
     HisLysSerArgMetTyrSerGlnCysValArgMetArgHisLeuSerGlnGluPheGly

4261 TGGCTCCAAATCACCCCCCAGGAATTCCTGTGCATGAAAGCACTGCTACTCTTCAGCATT
     TrpLeuGlnIleThrProGlnGluPheLeuCysMetLysAlaLeuLeuLeuPheSerIle

4321 ATTCCAGTGGATGGGCTGAAAAATCAAAAATTCTTTGATGAACTTCGAATGAACTACATC
     IleProValAspGlyLeuLysAsnGlnLysPhePheAspGluLeuArgMetAsnTyrIle

4381 AAGGAACTCGATCGTATCATTGCATGCAAAAGAAAAAATCCCACATCCTGCTCAAGACGC
     LysGluLeuAspArgIleIleAlaCysLysArgLysAsnProThrSerCysSerArgArg

4441 TTCTACCAGCTCACCAAGCTCCTGGACTCCGTGCAGCCTATTGCGAGAGAGCTGCATCAG
     PheTyrGlnLeuThrLysLeuLeuAspSerValGlnProIleAlaArgGluLeuHisGln

*FIG. 5D*

4501 TTCACTTTTGACCTGCTAATCAAGTCACACATGGTGAGCGTGGACTTTCCGGAAATGATG
     PheThrPheAspLeuLeuIleLysSerHisMetValSerValAspPheProGluMetMet

4561 GCAGAGATCATCTCTGTGCAAGTGCCCAAGATCCTTTCTGGGAAAGTCAAGCCCATCTAT
     AlaGluIleIleSerValGlnValProLysIleLeuSerGlyLysValLysProIleTyr

4621 TTCCACACCCAGTGAAGCATTGGAAACCCTATTTCCCCACCCCAGCTCATGCCCCCTTTC
     PheHisThrGlnEnd

4681 AGATGTCTTCTGCCTGTTATAACTCTGCACTACTCCTCTGCAGTGCCTTGGGGAATTTCC

4741 TCTATTGATGTACAGTCTGTCATGAACATGTTCCTGAATTCTATTTGCTGGGCTTTTTTT

4801 TTCTCTTTCTCTCCTTTCTTTTTCTTCTTCCCTCCCTATCTAACCCTCCCATGGCACCTT

4861 CAGACTTTGCTTCCCATTGTGGCTCCTATCTGTGTTTTGAATGGTGTTGTATGCCTTTAA

4921 ATCTGTGATGATCCTCATATGGCCCAGTGTCAAGTTGTGCTTGTTTACAGCACTACTCTG

4981 TGCCAGCCACACAAACGTTTACTTATCTTATGCCACGGGAAGTTTAGAGAGCTAAGATTA

5041 TCTGGGGAAATCAAAACAAAAAACAAGCAAACAAAAAAAAAA 5082

*FIG. 5E*

AATTCGGGAAGGATCGAGCAAACCAGGAAAGTAAGGATGGAGATCCTAGGAGAGTGTCCA 60

TGCCTCGAAAGGAGCCCACCAAAGATGAACTGTTGCATTTGCTTTCCACCTCCCAGCGCC 120

CCCTCGGAGATCCCTAGGAGCCAGCCTGCTGGGAGAACCAGAGGGTCCGGAGCAAACCTG 180

GAGGCTGAGAGGGCATCAGAGGGGAAAAGACTGAGTTAGCCACTCCAGTGCCATACAGAA 240

GCTTAAGGGACATACCACGCCAGCCCCAGCCCAGCGACAGCCAACGCCTGTTGCAGAGCG 300

GCGGCTTCGAAGCCGCCGCCCAGAAGCTGCCCTTTCCTCTTCGGTGAAGTTTCTAAAAGC 360

TGCGGGAGACTCGGAGGAAGCGAAGAAAGTGTCCGGTAGGACTACGACTGCCTTTGTCCT 420

CCTCCCTCCTACCCCTACCCCTCCTGGGTCCCTCTCCCTGAGCGGACTAGGCAGGCTTC 480

CTGGCCAGCCCTCTCCCCTACACCACCAGCTCTGCCAGCCAGTTTGCACAGAGGTAACTC 540

CCTTTGGCTGAAAGCAGACGAGCTTGTTGCCCATTGGAAGGGAGGCTTTTGGGAGCCCAG 600

AGACTGAGGAGCAACAGCACGCTGGAGAGTCCCTGATTCCAGGTTCTCCCCCCTGCACCT 660

CCTACTGCCCGCCCCTCACCCTGTGTGTGCAGCTAGAATTGAAAAGATGAAAAGACAGTT 720

GGGGCTTCAGTAGTCGAAAGCAAAACAAAAGCAAAAAGAAAACAAAAAGAAAATAGCCCA 780

GTTCTTATTTGCACCTGCTTCAGTGGACATTGACTTTGGAAGGCAGAGAATTTTCCTTCC 840

CCCCAGTCAAGCTTTGAGCATCTTTTAATCTGTTCTTCAAGTATTTAGGGACAAACTGTG 900

AAACTAGCAGGGCAGATCCTGTCTAGCGCGTGCCTTCCTTTACAGGAGACTTTGAGGCTA 960

TCTGGGCGCTCCCCCCCCTCCCTGCAAGTTTTCTTCCCTGGAGCTTCCCGCAGGTGGGCA 1020

GCTAGCTGCAGATACTACATCATCAGTCAGTAGAACTCTTCAGAGCAAGAGACGAGGAGG 1080

CAGGATAAGGGAATTCGGTGGAAGCTAGAGACAAGCTAAAGGATGGAGGTGCAGTTAGGG 1140
                                            MetGluValGlnLeuGly

CTGGGAAGGGTCTACCCACGGCCCCGTCCAAGACCTATCGAGGAGCGTTCCAGAATCTG 1200
LeuGlyArgValTyrProArgProProSerLysThrTyrArgGlyAlaPheGlnAsnLeu

TTCCAGAGCGTGCGCGAAGCGATCCAGAACCCGGGCCCCAGGCACCCTGAGGCCGCTAGC 1260
PheGlnSerValArgGluAlaIleGlnAsnProGlyProArgHisProGluAlaAlaSer

ATAGCACCTCCCGGTGCCTGTTTACAGCAGCGGCAGGAGACTAGCCCCGGCGGCGGCGG 1320
IleAlaProProGlyAlaCysLeuGlnGlnArgGlnGluThrSerProArgArgArgArg

CGGCAGCAGCACCCTGAGGATGGCTCTCCTCAAGCCCACATCAGAGGCACCACAGGCTAC 1380
ArgGlnGlnHisProGluAspGlySerProGlnAlaHisIleArgGlyThrThrGlyTyr

*FIG. 6A*

```
CTGGCCCTGGAGGAGGAACAGCAGCCTTCACAGCAGCAGTCAGCCTCCGAGGGCCACCCT 1440
LeuAlaLeuGluGluGluGlnGlnProSerGlnGlnGlnSerAlaSerGluGlyHisPro

GAGAGCGGCTGCCTCCCGGAGCCTGGAGCTGCCACGGCTCCTGGCAAGGGGCTGCCGCAG 1500
GluSerGlyCysLeuProGluProGlyAlaAlaThrAlaProGlyLysGlyLeuProGln

CAGCCACCAGCTCCTCCAGATCAGGATGACTCAGCTGCCCCATCCACGTTGTCCCTACTG 1560
GlnProProAlaProProAspGlnAspAspSerAlaAlaProSerThrLeuSerLeuLeu

GGCCCCACTTTCCCAGGCTTAAGCAGCTGCTCCGCAGACATTAAAGACATCCTGAGCGAG 1620
GlyProThrPheProGlyLeuSerSerCysSerAlaAspIleLysAspIleLeuSerGlu

GCCGGCACCATGCAACTTCTTCAGCAGCAGCAGCAACAGCAACAGCAGCAGCAGCAGCAG 1680
AlaGlyThrMetGlnLeuLeuGlnGlnGlnGlnGlnGlnGlnGlnGlnGlnGlnGlnGln

CAGCAGCAGCAGCAGCAACAGCAGCAGGAGGTAATATCCGAAGGCAGCAGCAGCGTGAGA 1740
GlnGlnGlnGlnGlnGlnGlnGlnGlnGluValIleSerGluGlySerSerSerValArg

GCAAGGGAGGCCACTGGGGCTCCCTCTTCCTCCAAGGATAGTTACCTAGGGGGCAATTCG 1800
AlaArgGluAlaThrGlyAlaProSerSerSerLysAspSerTyrLeuGlyGlyAsnSer

ACCATATCTGACAGTGCCAAGGAGTTGTGTAAAGCAGTGTCTGTGTCCATGGGGTTGGGT 1860
ThrIleSerAspSerAlaLysGluLeuCysLysAlaValSerValSerMetGlyLeuGly

GTGGAAGCACTGGAACATCTGAGTCCAGGGGAGCAGCTTCGGGGCGACTGCATGTACGCG 1920
ValGluAlaLeuGluHisLeuSerProGlyGluGlnLeuArgGlyAspCysMetTyrAla

TCGCTCCTGGGAGGTCCACCCGCCGTGCGTCCCACTCCTTGTGCGCCTCTGGCCGAATGC 1980
SerLeuLeuGlyGlyProProAlaValArgProThrProCysAlaProLeuAlaGluCys

AAAGGTCTTTCCCTGGACGAAGGCCCGGGCAAAGGCACTGAAGAGACTGCTGAGTATTCC 2040
LysGlyLeuSerLeuAspGluGlyProGlyLysGlyThrGluGluThrAlaGluTyrSer

TCTTTCAAGGGAGGTTACGCCAAAGGGTTGGAAGGTGAGAGTCTGGGCTGCTCTGGCAGC 2100
SerPheLysGlyGlyTyrAlaLysGlyLeuGluGlyGluSerLeuGlyCysSerGlySer

AGTGAAGCAGGTAGCTCTGGGACACTTGAGATCCCGTCCTCACTGTCTCTGTATAAGTCT 2160
SerGluAlaGlySerSerGlyThrLeuGluIleProSerSerLeuSerLeuTyrLysSer

GGAGCAGTAGACGAGGCAGCAGCATACCAGAATCGCGACTACTACAACTTTCCGCTCGCT 2220
GlyAlaValAspGluAlaAlaAlaTyrGlnAsnArgAspTyrTyrAsnPheProLeuAla

CTGTCCGGGCCGCCGCACCCCCCGCCCCCTACCCATCCACACGCCCGCATCAAGCTGGAG 2280
LeuSerGlyProProHisProProProThrHisProHisAlaArgIleLysLeuGlu

AACCCGTCGGACTACGGCAGCGCCTGGGCTGCGGCGGCAGCGCAATGCCGCTATGGGGAC 2340
AsnProSerAspTyrGlySerAlaTrpAlaAlaAlaAlaAlaGlnCysArgTyrGlyAsp

TTGGCTAGCCTACATGGAGGGAGTGTAGCCGGACCCAGCACTGGATCGCCCCCAGCCACC 2400
LeuAlaSerLeuHisGlyGlySerValAlaGlyProSerThrGlySerProProAlaThr
```

FIG. 6B

```
GCCTCTTCTTCCTGGCATACTCTCTTCACAGCTGAAGAAGGCCAATTATATGGGCCAGGA  2460
AlaSerSerSerTrpHisThrLeuPheThrAlaGluGluGlyGlnLeuTyrGlyProGly

GGCGGGGGCGGCAGCAGTAGCCCAAGCGATGCTGGGCCTGTAGCCCCCTATGGCTACACT  2520
GlyGlyGlyGlySerSerSerProSerAspAlaGlyProValAlaProTyrGlyTyrThr

CGGCCCCCTCAGGGGCTGGCAAGCCAGGAGGGTGACTTCTCTGCCTCTGAAGTGTGGTAT  2580
ArgProProGlnGlyLeuAlaSerGlnGluGlyAspPheSerAlaSerGluValTrpTyr

CCTGGTGGAGTTGTGAACAGAGTCCCCTATCCCAGTCCCAGTTGTGTTAAAAGTGAAATG  2640
ProGlyGlyValValAsnArgValProTyrProSerProSerCysValLysSerGluMet

GGACCTTGGATGGAGAACTACTCCGGACCTTATGGGGACATGCGTTTGGACAGTACCAGG  2700
GlyProTrpMetGluAsnTyrSerGlyProTyrGlyAspMetArgLeuAspSerThrArg

GACCACGTTTTACCCATCGACTATTACTTCCCACCCCAGAAGACCTGCCTGATCTGTGGA  2760
AspHisValLeuProIleAspTyrTyrPheProProGlnLysThrCysLeuIleCysGly

GATGAAGCTTCTGGTTGTCACTACGGAGCTCTCACTTGTGGCAGCTGCAAGGTCTTCTTC  2820
AspGluAlaSerGlyCysHisTyrGlyAlaLeuThrCysGlySerCysLysValPhePhe

AAAAGAGCTGCGGAAGGGAAACAGAAGTATCTATGTGCCAGCAGAAATGATTGCACCATT  2880
LysArgAlaAlaGluGlyLysGlnLysTyrLeuCysAlaSerArgAsnAspCysThrIle

GATAAATTTCGGAGGAAAAATTGTCCATCGTGTCGTCTCCGGAAATGTTATGAAGCAGGG  2940
AspLysPheArgArgLysAsnCysProSerCysArgLeuArgLysCysTyrGluAlaGly

ATGACTCTGGGAGCTCGTAAGCTGAAGAAACTTGGAAATCTCAAACTACAGGAAGAAGGA  3000
MetThrLeuGlyAlaArgLysLeuLysLysLeuGlyAsnLeuLysLeuGlnGluGluGly

GAAAACTCCAGTGCTGGTAGCCCCACTGAGGACCCATCCCAGAAGATGACTGTATCACAC  3060
GluAsnSerSerAlaGlySerProThrGluAspProSerGlnLysMetThrValSerHis

ATTGAAGGCTATGAATGTCAACCTATCTTTCTTAATGTCCTGGAAGCCATTGAGCCAGGA  3120
IleGluGlyTyrGluCysGlnProIlePheLeuAsnValLeuGluAlaIleGluProGly

GTGGTGTGTGCCGGACATGACAACAACCAGCCTGATTCCTTTGCTGCCTTGTTATCTAGT  3180
ValValCysAlaGlyHisAspAsnAsnGlnProAspSerPheAlaAlaLeuLeuSerSer

CTCAACGAGCTTGGCGAGAGACAGCTTGTACATGTGGTCAAGTGGGCCAAGGCCTTGCCT  3240
LeuAsnGluLeuGlyGluArgGlnLeuValHisValValLysTrpAlaLysAlaLeuPro

GGCTTCCGCAACTTGCATGTGGATGACCAGATGGCAGTCATTCAGTATTCTGGATGGGA  3300
GlyPheArgAsnLeuHisValAspAspGlnMetAlaValIleGlnTyrSerTrpMetGly

CTGATGGTATTTGCCATGGGTTGGCGGTCCTTCACTAATGTCAACTCTAGGATGCTCTAC  3360
LeuMetValPheAlaMetGlyTrpArgSerPheThrAsnValAsnSerArgMetLeuTyr

TTTGCACCTGACCTGGTTTTCAATGAGTATCGCATGCACAAGTCTCGAATGTACAGCCAG  3420
PheAlaProAspLeuValPheAsnGluTyrArgMetHisLysSerArgMetTyrSerGln
```

*FIG. 6C*

```
TGCGTGAGGATGAGGCACCTTTCTCAAGAGTTTGGATGGCTCCAGATAACCCCCCAGGAA  3480
CysValArgMetArgHisLeuSerGlnGluPheGlyTrpLeuGlnIleThrProGlnGlu

TTCCTGTGCATGAAAGCACTGCTACTCTTCAGCATTATTCCAGTGGATGGGCTGAAAAAT  3540
PheLeuCysMetLysAlaLeuLeuLeuPheSerIleIleProValAspGlyLeuLysAsn

CAAAAATTCTTTGATGAACTTCGAATGAACTACATCAAGGAACTTGATCGCATCATTGCA  3600
GlnLysPhePheAspGluLeuArgMetAsnTyrIleLysGluLeuAspArgIleIleAla

TGCAAAAGAAAAAATCCCACATCCTGCTCAAGGCGCTTCTACCAGCTCACCAAGCTCCTG  3660
CysLysArgLysAsnProThrSerCysSerArgArgPheTyrGlnLeuThrLysLeuLeu

GATTCTGTGCAGCCTATTGCAAGAGAGCTGCATCAATTCACTTTTGACCTGCTAATCAAG  3720
AspSerValGlnProIleAlaArgGluLeuHisGlnPheThrPheAspLeuLeuIleLys

TCCCATATGGTGAGCGTGGACTTTCCTGAAATGATGGCAGAGATCATCTCTGTGCAAGTG  3780
SerHisMetValSerValAspPheProGluMetMetAlaGluIleIleSerValGlnVal

CCCAAGATCCTTTCTGGGAAAGTCAAGCCCATCTATTTCCACACACAGTGAAGATTTGGA  3840
ProLysIleLeuSerGlyLysValLysProIleTyrPheHisThrGlnEnd

ACCTAATACCCAAACCCACCTGTTCCCTTTTCAGATGTCTTCTGCCTGTTATATAACTCT  3900

GCACTACTTCTCTGGCATGGGCCTTGGGGGAAATTCCTCTACTGATGTACAGTCTGTCAT  3960

GAACATGTTCCCCAAGTTCTATTTCCTGGGCTTTTCCTTCTTTCTTTTCTTCTTCTCTG  4020

CCTCTTTTACCCTCCCATGGCACATTTTGAATCCGCTGCGTGTTGTGGCTCCTGCCTGTG  4080

TTTTGAGTTTTGTTGTATTTCTTCAAGTCTGTGATGATCTTCTTGTGGCCCAGTGTCAAC  4140

TGTGCTTGTTTATAGCACTGTGCTGTGTGCCAACCAAGCAAATGTTTACTCACCTTATGC  4200

CATGGCAAGTTTAGAGAGCTATAAGTATCTTGGGAAGAAACAAACAGAGAGAGTAAAAAA  4260

ACCAAAAAAAAAAAAAAAAAAACCGAATTC                                4289
```

*FIG. 6D*

SEQUENCE LISTING

<160> NUMBER OF SEQ ID NOS: 26

<210> SEQ ID NO 1
<211> LENGTH: 32
<212> TYPE: DNA
<213> ORGANISM: Artificial Sequence
<220> FEATURE:
<223> OTHER INFORMATION: Synthetic Oligonucleotide probe.

<400> SEQUENCE: 1
acctgtgagg gctgtaaggt cttcttcaaa ag                          32

<210> SEQ ID NO 2
<211> LENGTH: 32
<212> TYPE: DNA
<213> ORGANISM: Homo sapiens

<400> SEQUENCE: 2
acatgtggaa gctgcaaggt cttcttcaaa ag                          32

<210> SEQ ID NO 3
<211> LENGTH: 32
<212> TYPE: DNA
<213> ORGANISM: Homo sapiens

<400> SEQUENCE: 3

```
acctgtggga gctgtaaggt cttctttaag ag                                       32

<210> SEQ ID NO 4
<211> LENGTH: 32
<212> TYPE: DNA
<213> ORGANISM: Homo sapiens

<400> SEQUENCE: 4
acctgtggca gctgcaaagt tttcttcaaa ag                                       32

<210> SEQ ID NO 5
<211> LENGTH: 32
<212> TYPE: DNA
<213> ORGANISM: Homo sapiens

<400> SEQUENCE: 5
acttgtggaa gctgtaaagt tttcttcaaa ag                                       32

<210> SEQ ID NO 6
<211> LENGTH: 32
<212> TYPE: DNA
<213> ORGANISM: Homo sapiens

<400> SEQUENCE: 6
tcctgtgagg gctgtaaggc cttcttcaag ag                                       32

<210> SEQ ID NO 7
<211> LENGTH: 32
<212> TYPE: DNA
<213> ORGANISM: Homo sapiens

<400> SEQUENCE: 7
acgtgtgaag gctgcaaggg tttctttaga ag                                       32

<210> SEQ ID NO 8
<211> LENGTH: 32
<212> TYPE: DNA
<213> ORGANISM: Homo sapiens

<400> SEQUENCE: 8
gcctgtgagg gctgcaaggg cttcttccgc cg                                       32

<210> SEQ ID NO 9
<211> LENGTH: 66
<212> TYPE: PRT
<213> ORGANISM: Homo sapiens

<400> SEQUENCE: 9

Cys Leu Ile Cys Gly Asp Glu Ala Ser Gly Cys His Tyr Gly Ala Leu
1               5                   10                  15

Thr Cys Gly Ser Cys Lys Val Phe Phe Lys Arg Ala Ala Glu Gly Lys
            20                  25                  30

Gln Lys Tyr Leu Cys Ala Ser Arg Asn Asp Cys Thr Ile Asp Lys Phe
        35                  40                  45

Arg Arg Lys Asn Cys Pro Ser Cys Arg Leu Arg Lys Cys Tyr Glu Ala
    50                  55                  60

Gly Met
65

<210> SEQ ID NO 10
<211> LENGTH: 66
```

```
<212> TYPE: PRT
<213> ORGANISM: Homo sapiens

<400> SEQUENCE: 10

Cys Leu Ile Cys Gly Asp Glu Ala Ser Gly Cys His Tyr Gly Val Leu
1               5                   10                  15

Thr Cys Gly Ser Cys Lys Val Phe Phe Lys Arg Ala Met Glu Gly Gln
            20                  25                  30

His Asn Tyr Leu Cys Ala Gly Arg Asn Asp Cys Ile Val Asp Lys Ile
        35                  40                  45

Arg Arg Lys Asn Cys Pro Ala Cys Arg Leu Arg Lys Cys Cys Gln Ala
    50                  55                  60

Gly Met
65

<210> SEQ ID NO 11
<211> LENGTH: 66
<212> TYPE: PRT
<213> ORGANISM: Homo sapiens

<400> SEQUENCE: 11

Cys Leu Val Cys Gly Asp Glu Ala Ser Gly Cys His Tyr Gly Val Val
1               5                   10                  15

Thr Cys Gly Ser Cys Lys Val Phe Phe Lys Arg Ala Val Glu Gly Gln
            20                  25                  30

His Asn Tyr Leu Cys Ala Gly Arg Asn Asp Cys Ile Ile Asp Lys Ile
        35                  40                  45

Arg Arg Lys Asn Cys Pro Ala Cys Arg Leu Gln Lys Cys Leu Gln Ala
    50                  55                  60

Gly Met
65

<210> SEQ ID NO 12
<211> LENGTH: 66
<212> TYPE: PRT
<213> ORGANISM: Homo sapiens

<400> SEQUENCE: 12

Cys Leu Val Cys Ser Asp Glu Ala Ser Gly Cys His Tyr Gly Val Leu
1               5                   10                  15

Thr Cys Gly Ser Cys Lys Val Phe Phe Lys Arg Ala Val Glu Gly Gln
            20                  25                  30

His Asn Tyr Leu Cys Ala Gly Arg Asn Asp Cys Ile Ile Asp Lys Ile
        35                  40                  45

Arg Arg Lys Asn Cys Pro Ala Cys Arg Tyr Arg Lys Cys Leu Gln Ala
    50                  55                  60

Gly Met
65

<210> SEQ ID NO 13
<211> LENGTH: 66
<212> TYPE: PRT
<213> ORGANISM: Homo sapiens

<400> SEQUENCE: 13

Cys Ala Val Cys Asn Asp Tyr Ala Ser Gly Tyr His Tyr Gly Val Trp
1               5                   10                  15

Ser Cys Glu Gly Cys Lys Ala Phe Phe Lys Arg Ser Ile Gln Gly His
            20                  25                  30
```

```
Asn Asp Tyr Met Cys Pro Ala Thr Asn Gln Cys Thr Ile Asp Lys Asn
        35                  40                  45

Arg Arg Lys Ser Cys Gln Ala Cys Arg Leu Arg Lys Cys Tyr Glu Val
    50                  55                  60

Gly Met
65

<210> SEQ ID NO 14
<211> LENGTH: 66
<212> TYPE: PRT
<213> ORGANISM: Gallus gallus

<400> SEQUENCE: 14

Cys Gly Val Cys Gly Asp Arg Ala Thr Gly Phe His Phe Asn Ala Met
1               5                   10                  15

Thr Cys Glu Gly Cys Lys Gly Phe Phe Arg Arg Ser Met Lys Arg Lys
            20                  25                  30

Ala Met Phe Thr Cys Pro Phe Asn Gly Asp Cys Lys Ile Thr Lys Asp
        35                  40                  45

Asn Arg Arg His Cys Gln Ala Cys Arg Leu Lys Arg Cys Val Asp Ile
    50                  55                  60

Gly Met
65

<210> SEQ ID NO 15
<211> LENGTH: 68
<212> TYPE: PRT
<213> ORGANISM: Homo sapiens

<400> SEQUENCE: 15

Cys Val Val Cys Gly Asp Lys Ala Thr Gly Tyr His Tyr Arg Cys Ile
1               5                   10                  15

Thr Cys Glu Gly Cys Lys Gly Phe Phe Arg Arg Thr Ile Gln Lys Asn
            20                  25                  30

Leu His Pro Ser Tyr Ser Cys Lys Tyr Glu Gly Lys Cys Val Ile Asp
        35                  40                  45

Lys Val Thr Arg Asn Gln Cys Gln Glu Cys Arg Phe Lys Lys Cys Ile
    50                  55                  60

Tyr Val Gly Met
65

<210> SEQ ID NO 16
<211> LENGTH: 68
<212> TYPE: PRT
<213> ORGANISM: Avian erythroblastosis virus

<400> SEQUENCE: 16

Cys Val Val Cys Gly Asp Lys Ala Thr Gly Tyr His Tyr Arg Cys Ile
1               5                   10                  15

Thr Cys Glu Gly Cys Lys Ser Phe Phe Arg Arg Thr Ile Gln Lys Asn
            20                  25                  30

Leu His Pro Thr Thr Ser Cys Thr Tyr Asp Gly Cys Cys Val Ile Asp
        35                  40                  45

Lys Ile Thr Arg Asn Gln Cys Gln Leu Cys Arg Phe Lys Lys Cys Ile
    50                  55                  60

Ser Val Gly Met
65
```

<210> SEQ ID NO 17
<211> LENGTH: 66
<212> TYPE: PRT
<213> ORGANISM: Homo sapiens

<400> SEQUENCE: 17

Cys Phe Val Cys Gln Asp Lys Ser Ser Gly Tyr His Tyr Gly Val Ser
1               5                   10                  15

Ala Cys Glu Gly Cys Lys Gly Phe Phe Arg Arg Ser Ile Gln Lys Asn
            20                  25                  30

Met Val Tyr Thr Cys His Arg Asp Lys Asn Cys Ile Ile Asn Lys Val
        35                  40                  45

Thr Arg Asn Arg Cys Gln Tyr Cys Arg Leu Gln Lys Cys Phe Glu Val
    50                  55                  60

Gly Met
65

<210> SEQ ID NO 18
<211> LENGTH: 5082
<212> TYPE: DNA
<213> ORGANISM: Homo sapiens
<220> FEATURE:
<221> NAME/KEY: misc_feature
<222> LOCATION: (360)..(360)
<223> OTHER INFORMATION: "n" denotes any nucleotide.
<220> FEATURE:
<221> NAME/KEY: misc_feature
<222> LOCATION: (365)..(365)
<223> OTHER INFORMATION: "n" denotes any nucleotide.
<220> FEATURE:
<221> NAME/KEY: misc_feature
<222> LOCATION: (376)..(376)
<223> OTHER INFORMATION: "n" denotes any nucleotide.
<220> FEATURE:
<221> NAME/KEY: misc_feature
<222> LOCATION: (385)..(385)
<223> OTHER INFORMATION: "n" denotes any nucleotide.
<220> FEATURE:
<221> NAME/KEY: misc_feature
<222> LOCATION: (399)..(399)
<223> OTHER INFORMATION: "n" denotes any nucleotide.
<220> FEATURE:
<221> NAME/KEY: misc_feature
<222> LOCATION: (407)..(407)
<223> OTHER INFORMATION: "n" denotes any nucleotide.
<220> FEATURE:
<221> NAME/KEY: misc_feature
<222> LOCATION: (417)..(417)
<223> OTHER INFORMATION: "n" denotes any nucleotide.
<220> FEATURE:
<221> NAME/KEY: misc_feature
<222> LOCATION: (422)..(422)
<223> OTHER INFORMATION: "n" denotes any nucleotide.
<220> FEATURE:
<221> NAME/KEY: misc_feature
<222> LOCATION: (435)..(435)
<223> OTHER INFORMATION: "n" denotes any nucleotide.
<220> FEATURE:
<221> NAME/KEY: misc_feature
<222> LOCATION: (439)..(439)
<223> OTHER INFORMATION: "n" denotes any nucleotide.
<220> FEATURE:
<221> NAME/KEY: misc_feature
<222> LOCATION: (441)..(441)
<223> OTHER INFORMATION: "n" denotes any nucleotide.
<220> FEATURE:
<221> NAME/KEY: misc_feature
<222> LOCATION: (598)..(598)
<223> OTHER INFORMATION: "n" denotes any nucleotide.
<220> FEATURE:
<221> NAME/KEY: misc_feature
<222> LOCATION: (689)..(689)

```
<223> OTHER INFORMATION: "n" denotes any nucleotide.
<220> FEATURE:
<221> NAME/KEY: misc_feature
<222> LOCATION: (714)..(715)
<223> OTHER INFORMATION: "n" denotes any nucleotide.
<220> FEATURE:
<221> NAME/KEY: misc_feature
<222> LOCATION: (844)..(844)
<223> OTHER INFORMATION: "n" denotes any nucleotide.
<220> FEATURE:
<221> NAME/KEY: misc_feature
<222> LOCATION: (870)..(870)
<223> OTHER INFORMATION: "n" denotes any nucleotide.
<220> FEATURE:
<221> NAME/KEY: misc_feature
<222> LOCATION: (918)..(918)
<223> OTHER INFORMATION: "n" denotes any nucleotide.
<220> FEATURE:
<221> NAME/KEY: misc_feature
<222> LOCATION: (932)..(932)
<223> OTHER INFORMATION: "n" denotes any nucleotide.
<220> FEATURE:
<221> NAME/KEY: misc_feature
<222> LOCATION: (1195)..(1195)
<223> OTHER INFORMATION: "n" denotes any nucleotide.
<220> FEATURE:
<221> NAME/KEY: misc_feature
<222> LOCATION: (1198)..(1198)
<223> OTHER INFORMATION: "n" denotes any nucleotide.
<220> FEATURE:
<221> NAME/KEY: misc_feature
<222> LOCATION: (1202)..(1202)
<223> OTHER INFORMATION: "n" denotes any nucleotide.
<220> FEATURE:
<221> NAME/KEY: misc_feature
<222> LOCATION: (1248)..(1248)
<223> OTHER INFORMATION: "n" denotes any nucleotide.
<220> FEATURE:
<221> NAME/KEY: misc_feature
<222> LOCATION: (1322)..(1322)
<223> OTHER INFORMATION: "n" denotes any nucleotide.

<400> SEQUENCE: 18
gagctctgga caaaattgag cgcctatgtg tacatggcaa gtgtttttag tgtttgtgtg      60
tttacctgct tgtctgggtg attttgcctt tgagagtctg gatgagaaat gcatggttaa     120
aggcaattcc agacaggaag aaaggcagag aagagggtag aaatgacctc tgattcttgg     180
ggctgagggt tcctagagca aatggcacaa tgccacgagg cccgatctat ccctatgacg     240
gaactctaag gtttcagcat cagctatctg ctggcttggt cactggcttg cctcctcagt     300
ttgtaggaga ctctcccact ctcccatctg cgcgctctta tcagtcctga aaagaacccn     360
tggcnagcca ggagcnaggt attcntatcg tccttttcnt cctcctngcc tcacctngtt     420 gnttttttaga ttggncttng naaccaaatt tgtatgctgg cctccaggaa atctggagcc     480
tggcgcctaa accttggttt aggaaagcag gagctattca ggaagcaggg tcctccaggg     540
ctagagctag cctctcctgc cctcgcccac gtgcgccagc acttgtttct ccaaagcnac     600
taggcaggcg ttagcgcgcg gtgagggag gggagaaaag gaaaggggag gggagggaaa     660
aggaggtggg aaggcaagga ggccggccng gtggggcgg gacccgactc gcannaactg     720
ttgcatttgc tctccacctc ccagcgcccc tccgagatc ccgggagcc agcttgctgg     780 gagagcggga acggtccgga gcaagcccag aggcagagga ggcgacagag ggaaaaaggg     840
cccnagctag ccgctccagt gctgtacagn agccgaagga cgcaccacgc cagccccagc     900
ccggctccag cgacagcnaa cgcctcttgc angcgttcga agccgccgcc cggagctgcc     960 cttttcctctt cggtgaagtt tttaaaagct gctaaagact cggaggaagc aaggaaagtg    1020
cctggtagga ctgacggctg cctttgtcct cctcctctcc acccgcctc ccccaccct     1080
```

-continued

```
gccttccccc cctccccccgt cttctctccc gcagctgcct cagtcggcta ctctcagcca    1140
accccccctca ccaccttct ccccacccgc cccccgccc ccgtcggccc agcgntgnca      1200
gnccgagttt gcagagaggt aactcccttt ggctgcgagc gggcgagnct agctgcacat    1260
tgcaaagaag gctcttagga gcaggcgact ggggagcggc ttcagcactg cagccacgac    1320
cngcctggtt aggctgcacg cggagagaac cctctgtttt ccccactct ctctccacct     1380
cctcctgcct tccccacccc gagtgcggag ccagagatca aaagatgaaa aggcagtcag    1440
gtcttcagta gccaaaaaac aaaacaaaca aaaacaaaaa agccgaaata aagaaaaag     1500
ataataactc agttcttatt tgcacctact tcagtggaca ctgaatttgg aaggtggagg    1560
attttgtttt tttcttttaa gatctgggca tcttttgaat ctaccttca agtattaaga     1620
acagactgt gagcctagca gggcagatct tgtccaccgt gtgtcttctt ctgcacgaga     1680
ctttgaggct gtcagagcgc ttttgcgtg gttgctcccg caagtttcct tctctggagc     1740
ttcccgcagg tgggcagcta gctgcagcga ctaccgcatc atcacagcct gttgaactct    1800
tctgagcaag agaaggggag gcggggtaag ggaagtaggt ggaagattca gccaagctca    1860
aggatggaag tgcagttagg gctgggaagg gtctaccctc ggccgccgtc caagacctac    1920
cgaggagctt tccagaatct gttccagagc gtgcgcgaag tgatccagaa cccgggcccc    1980
aggcacccag aggccgcgag cgcagcacct cccggcgcca gtttgctgct gctgcagcag    2040
cagcagcagc agcagcagca gcagcagcag cagcagcagc agcagcagca gcagcagcag    2100
cagcagcaag agactagccc caggcagcag cagcagcagc agggtgagga tggttctccc    2160
caagcccatc gtagaggccc cacaggctac ctggtcctgg atgaggaaca gcaaccttca    2220
cagccgcagt cggccctgga gtgccacccc gagagaggtt gcgtcccaga gcctggagcc    2280
gccgtggccg ccagcaaggg gctgccgcag cagctgccag cacctccgga cgaggatgac    2340
tcagctgccc catccacgtt gtccctgctg ggccccactt tccccggctt aagcagctgc    2400
tccgctgacc ttaaagacat cctgagcgag gccagcacca tgcaactcct tcagcaacag    2460
cagcaggaag cagtatccga aggcagcagc agcgggagag cgagggaggc ctcgggggct    2520
cccacttcct ccaaggacaa ttacttaggg ggcacttcga ccatttctga caacgccaag    2580
gagttgtgta aggcagtgtc ggtgtccatg ggcctgggtg tggaggcgtt ggagcatctg    2640
agtccagggg aacagcttcg gggggattgc atgtacgccc cacttttggg agttccaccc    2700
gctgtgcgtc ccactccttg tgccccattg gccgaatgca aaggttctct gctagacgac    2760
agcgcaggca agagcactga agatactgct gagtattccc ctttcaaggg aggttacacc    2820
aaagggctag aaggcgagag cctaggctgc tctggcagcg ctgcagcagg agctccgggg    2880
acacttgaac tgccgtctac cctgtctctc tacaagtccg gagcactgga cgaggcagct    2940
gcgtaccaga gtcgcgacta ctacaacttt ccactggctc tggccggacc gccgccccct    3000
ccgccgcctc cccatcccca cgctcgcatc aagctggaga accgctggga ctacggcagc    3060
gcctgggcgg ctgcgcggc gcagtgccgc tatgggggacc tggcgagcct gcatggcgcg    3120
ggtgcagcgg gacccggttc tgggtcaccc tcagccgccg cttcctcatc ctggcacact    3180
ctcttcacag ccgaagaagg ccagttgtat ggaccgtgtg gtggtggtgg gggtggtggc    3240
ggcggcggcg gcggcggcgg cggcggcggc ggcggcggcg gcggcggcgg cgaggcggga    3300
gctgtagccc cctacggcta cactcggccc cctcagggc tggcgggcca ggaaagcgac    3360
ttcaccgcac ctgatgtgtg gtaccctggc ggcatggtga gcagagtgcc ctatcccagt    3420
```

-continued

```
cccacttgtg tcaaaagcga aatgggcccc tggatggata gctactccgg accttacggg    3480
gacatgcgtt tggagactgc cagggaccat gttttgccca ttgactatta ctttccaccc    3540
cagaagacct gcctgatctg tggagatgaa gcttctgggt gtcactatgg agctctcaca    3600
tgtggaagct gcaaggtctt cttcaaaaga gccgctgaag ggaaacagaa gtacctgtgc    3660
gccagcagaa atgattgcac tattgataaa ttccgaagga aaaattgtcc atcttgtcgt    3720
cttcggaaat gttatgaagc agggatgact ctggagcccg gaagctgaag aaacttggt     3780
aatctgaaac tacaggagga aggagaggct tccagcacca ccagcccac tgaggagaca     3840
acccagaagc tgacagtgtc acacattgaa ggctatgaat gtcagcccat ctttctgaat    3900
gtcctggaag ccattgagcc aggtgtagtg tgtgctggac acgacaacaa ccagcccgac    3960
tcctttgcag ccttgctctc tagcctcaat gaactgggag agacagct tgtacacgtg      4020
gtcaagtggg ccaaggcctt gcctggcttc cgcaacttac acgtggacga ccagatggct    4080
gtcattcagt actcctggat ggggctcatg gtgtttgcca tgggctggcg atccttcacc    4140
aatgtcaact ccaggatgct ctacttcgcc cctgatctgg ttttcaatga gtaccgcatg    4200
cacaagtccc ggatgtacag ccagtgtgtc cgaatgaggc acctctctca agagtttgga   4260
tggctccaaa tcaccccca ggaattcctg tgcatgaaag cactgctact cttcagcatt    4320
attccagtgg atgggctgaa aaatcaaaaa ttctttgatg aacttcgaat gaactacatc    4380
aaggaactcg atcgtatcat tgcatgcaaa agaaaaaatc ccacatcctg ctcaagacgc    4440
ttctaccagc tcaccaagct cctggactcc gtgcagccta ttgcgagaga gctgcatcag    4500
ttcactttg acctgctaat caagtcacac atggtgagcg tggactttcc ggaaatgatg   4560
gcagagatca tctctgtgca agtgcccaag atccttctg ggaaagtcaa gcccatctat     4620
ttccacaccc agtgaagcat tggaaaccct atttccccac cccagctcat gccccctttc    4680
agatgtcttc tgcctgttat aactctgcac tactcctctg cagtgccttg ggaatttcc    4740
tctattgatg tacagtctgt catgaacatg ttcctgaatt ctatttgctg ggctttttt     4800
ttctctttct ctccttttctt tttcttcttc cctcccatc taaccctccc atggcacctt    4860
cagactttgc ttcccattgt ggctcctatc tgtgttttga atggtgttgt atgcctttaa    4920
atctgtgatg atcctcatat ggcccagtgt caagttgtgc ttgtttacag cactactctg    4980
tgccagccac acaaacgttt acttatctta tgccacggga agtttagaga gctaagatta    5040
tctggggaaa tcaaaacaaa aaacaagcaa acaaaaaaaa aa                       5082
```

<210> SEQ ID NO 19
<211> LENGTH: 923
<212> TYPE: PRT
<213> ORGANISM: Homo sapiens

<400> SEQUENCE: 19

```
Met Glu Val Gln Leu Gly Leu Gly Arg Val Tyr Pro Arg Pro Pro Ser
1               5                   10                  15

Lys Thr Tyr Arg Gly Ala Phe Gln Asn Leu Phe Gln Ser Val Arg Glu
            20                  25                  30

Val Ile Gln Asn Pro Gly Pro Arg His Pro Glu Ala Ala Ser Ala Ala
        35                  40                  45

Pro Pro Gly Ala Ser Leu Leu Leu Leu Gln Gln Gln Gln Gln Gln Gln
    50                  55                  60

Gln Gln Gln Gln Gln Gln Gln Gln Gln Gln Gln Gln Gln Gln Gln Gln
65                  70                  75                  80
```

-continued

```
Gln Gln Glu Thr Ser Pro Arg Gln Gln Gln Gln Gln Gly Glu Asp
                85                  90                  95

Gly Ser Pro Gln Ala His Arg Arg Gly Pro Thr Gly Tyr Leu Val Leu
            100                 105                 110

Asp Glu Glu Gln Gln Pro Ser Gln Pro Gln Ser Ala Leu Glu Cys His
            115                 120                 125

Pro Glu Arg Gly Cys Val Pro Glu Pro Gly Ala Ala Val Ala Ala Ser
            130                 135                 140

Lys Gly Leu Pro Gln Gln Leu Pro Ala Pro Pro Asp Glu Asp Asp Ser
145                 150                 155                 160

Ala Ala Pro Ser Thr Leu Ser Leu Leu Gly Pro Thr Phe Pro Gly Leu
                165                 170                 175

Ser Ser Cys Ser Ala Asp Leu Lys Asp Ile Leu Ser Glu Ala Ser Thr
                180                 185                 190

Met Gln Leu Leu Gln Gln Gln Gln Glu Ala Val Ser Glu Gly Ser
        195                 200                 205

Ser Ser Gly Arg Ala Arg Glu Ala Ser Gly Ala Pro Thr Ser Ser Lys
    210                 215                 220

Asp Asn Tyr Leu Gly Gly Thr Ser Thr Ile Ser Asp Asn Ala Lys Glu
225                 230                 235                 240

Leu Cys Lys Ala Val Ser Val Ser Met Gly Leu Gly Val Glu Ala Leu
                245                 250                 255

Glu His Leu Ser Pro Gly Glu Gln Leu Arg Gly Asp Cys Met Tyr Ala
                260                 265                 270

Pro Leu Leu Gly Val Pro Pro Ala Val Arg Pro Thr Pro Cys Ala Pro
            275                 280                 285

Leu Ala Glu Cys Lys Gly Ser Leu Leu Asp Asp Ser Ala Gly Lys Ser
            290                 295                 300

Thr Glu Asp Thr Ala Glu Tyr Ser Pro Phe Lys Gly Gly Tyr Thr Lys
305                 310                 315                 320

Gly Leu Glu Gly Glu Ser Leu Gly Cys Ser Gly Ser Ala Ala Gly
                325                 330                 335

Ser Ser Gly Thr Leu Glu Leu Pro Ser Thr Leu Ser Leu Tyr Lys Ser
            340                 345                 350

Gly Ala Leu Asp Glu Ala Ala Tyr Gln Ser Arg Asp Tyr Tyr Asn
            355                 360                 365

Phe Pro Leu Ala Leu Ala Gly Pro Pro Pro Pro Pro Pro Pro His
370                 375                 380

Pro His Ala Arg Ile Lys Leu Glu Asn Pro Leu Asp Tyr Gly Ser Ala
385                 390                 395                 400

Trp Ala Ala Ala Ala Gln Cys Arg Tyr Gly Asp Leu Ala Ser Leu
                405                 410                 415

His Gly Ala Gly Ala Ala Gly Pro Gly Ser Gly Ser Pro Ser Ala Ala
            420                 425                 430

Ala Ser Ser Ser Trp His Thr Leu Phe Thr Ala Glu Glu Gly Gln Leu
    435                 440                 445

Tyr Gly Pro Cys Gly Gly Gly Gly Gly Gly Gly Gly Gly Gly Gly
            450                 455                 460

Gly Gly Gly Gly Gly Gly Gly Gly Gly Gly Glu Ala Gly Ala
465                 470                 475                 480

Val Ala Pro Tyr Gly Tyr Thr Arg Pro Pro Gln Gly Leu Ala Gly Gln
                485                 490                 495

Glu Ser Asp Phe Thr Ala Pro Asp Val Trp Tyr Pro Gly Gly Met Val
```

-continued

```
                500                 505                 510
Ser Arg Val Pro Tyr Pro Ser Pro Thr Cys Val Lys Ser Glu Met Gly
        515                 520                 525

Pro Trp Met Asp Ser Tyr Ser Gly Pro Tyr Gly Asp Met Arg Leu Glu
        530                 535                 540

Thr Ala Arg Asp His Val Leu Pro Ile Asp Tyr Tyr Phe Pro Pro Gln
545                 550                 555                 560

Lys Thr Cys Leu Ile Cys Gly Asp Glu Ala Ser Gly Cys His Tyr Gly
                565                 570                 575

Ala Leu Thr Cys Gly Ser Cys Lys Val Phe Phe Lys Arg Ala Ala Glu
            580                 585                 590

Gly Lys Gln Lys Tyr Leu Cys Ala Ser Arg Asn Asp Cys Thr Ile Asp
        595                 600                 605

Lys Phe Arg Arg Lys Asn Cys Pro Ser Cys Arg Leu Arg Lys Cys Tyr
    610                 615                 620

Glu Ala Gly Met Thr Leu Gly Ala Arg Lys Leu Lys Lys Leu Gly Asn
625                 630                 635                 640

Leu Lys Leu Gln Glu Glu Gly Glu Ala Ser Ser Thr Thr Ser Pro Thr
                645                 650                 655

Glu Glu Thr Thr Gln Lys Leu Thr Val Ser His Ile Glu Gly Tyr Glu
            660                 665                 670

Cys Gln Pro Ile Phe Leu Asn Val Leu Glu Ala Ile Glu Pro Gly Val
        675                 680                 685

Val Cys Ala Gly His Asp Asn Asn Gln Pro Asp Ser Phe Ala Ala Leu
    690                 695                 700

Leu Ser Ser Leu Asn Glu Leu Gly Glu Arg Gln Leu Val His Val Val
705                 710                 715                 720

Lys Trp Ala Lys Ala Leu Pro Gly Phe Arg Asn Leu His Val Asp Asp
                725                 730                 735

Gln Met Ala Val Ile Gln Tyr Ser Trp Met Gly Leu Met Val Phe Ala
            740                 745                 750

Met Gly Trp Arg Ser Phe Thr Asn Val Asn Ser Arg Met Leu Tyr Phe
        755                 760                 765

Ala Pro Asp Leu Val Phe Asn Glu Tyr Arg Met His Lys Ser Arg Met
    770                 775                 780

Tyr Ser Gln Cys Val Arg Met Arg His Leu Ser Gln Glu Phe Gly Trp
785                 790                 795                 800

Leu Gln Ile Thr Pro Gln Glu Phe Leu Cys Met Lys Ala Leu Leu Leu
                805                 810                 815

Phe Ser Ile Ile Pro Val Asp Gly Leu Lys Asn Gln Lys Phe Phe Asp
            820                 825                 830

Glu Leu Arg Met Asn Tyr Ile Lys Glu Leu Asp Arg Ile Ile Ala Cys
        835                 840                 845

Lys Arg Lys Asn Pro Thr Ser Cys Ser Arg Arg Phe Tyr Gln Leu Thr
    850                 855                 860

Lys Leu Leu Asp Ser Val Gln Pro Ile Ala Arg Glu Leu His Gln Phe
865                 870                 875                 880

Thr Phe Asp Leu Leu Ile Lys Ser His Met Val Ser Val Asp Phe Pro
                885                 890                 895

Glu Met Met Ala Glu Ile Ile Ser Val Gln Val Pro Lys Ile Leu Ser
            900                 905                 910

Gly Lys Val Lys Pro Ile Tyr Phe His Thr Gln
        915                 920
```

<210> SEQ ID NO 20
<211> LENGTH: 4288
<212> TYPE: DNA
<213> ORGANISM: Rattus rattus

<400> SEQUENCE: 20

| | | | | | | |
|---|---|---|---|---|---|---|
| aattcgggaa | ggatcgagca | aaccaggaaa | gtaaggatgg | agatcctagg | agagtgtcca | 60 |
| tgcctcgaaa | ggagcccacc | aaagatgaac | tgttgcattt | gctttccacc | tcccagcgcc | 120 |
| ccctcggaga | tccctaggag | ccagcctgct | gggagaacca | gagggtccgg | agcaaacctg | 180 |
| gaggctgaga | gggcatcaga | ggggaaaaga | ctgagttagc | cactccagtg | ccatacagaa | 240 |
| gcttaaggga | cataccacgc | cagcccagc | ccagcgacag | ccaacgcctg | ttgcagagcg | 300 |
| gcggcttcga | agccgccgcc | cagaagctgc | cctttcctct | tcggtgaagt | ttctaaaagc | 360 |
| tgcgggagac | tcggaggaag | cgaagaaagt | gtccggtagg | actacgactg | cctttgtcct | 420 |
| cctccctcct | accctaccc | ctcctgggtc | ccctctccct | gagcggacta | ggcaggcttc | 480 |
| ctggccagcc | ctctccccta | caccaccagc | tctgccagcc | agtttgcaca | gaggtaactc | 540 |
| cctttggctg | aaagcagacg | agcttgttgc | ccattggaag | ggaggctttt | gggagcccag | 600 |
| agactgagga | gcaacagcac | gctggagagt | ccctgattcc | aggttctccc | ccctgcacct | 660 |
| cctactgccc | gccccctcacc | ctgtgtgtgc | agctagaatt | gaaaagatga | aaagacagtt | 720 |
| ggggcttcag | tagtcgaaag | caaaacaaaa | gcaaaaagaa | aacaaaaaga | aaatagccca | 780 |
| gttcttattt | gcacctgctt | cagtggacat | tgactttgga | aggcagagaa | ttttccttcc | 840 |
| ccccagtcaa | gctttgagca | tcttttaatc | tgttcttcaa | gtatttaggg | acaaactgtg | 900 |
| aaactagcag | ggcagatcct | gtctagcgcg | tgccttcctt | tacaggagac | tttgaggcta | 960 |
| tctggcgct | ccccccctc | cctgcaagtt | ttcttccctg | gagcttcccg | caggtgggca | 1020 |
| gctagctgca | gatactacat | catcagtcag | tagaactctt | cagagcaaga | gacgaggagg | 1080 |
| caggataagg | gaattcggtg | gaagctagag | acaagctaaa | ggatggaggt | gcagttaggg | 1140 |
| ctgggaaggg | tctaccacg | gccccgtcc | aagacctatc | gaggagcgtt | ccagaatctg | 1200 |
| ttccagagcg | tgcgcgaagc | gatccagaac | ccgggcccca | ggcaccctga | ggccgctagc | 1260 |
| atagcacctc | ccgtgcctg | tttacagcag | cggcaggaga | ctagccccg | gcggcggcgg | 1320 |
| cggcagcagc | accctgagga | tggctctcct | caagcccaca | tcagaggcac | cacaggctac | 1380 |
| ctggccctgg | aggaggaaca | gcagccttca | cagcagcagt | cagcctccga | gggccaccct | 1440 |
| gagagcggct | gcctcccgga | gcctggagct | gccacggctc | ctggcaaggg | gctgccgcag | 1500 |
| cagccaccag | ctcctccaga | tcaggatgac | tcagctgccc | catccacgtt | gtccctactg | 1560 |
| ggccccactt | tcccaggctt | aagcagctgc | tccgcagaca | ttaaagacat | cctgagcgag | 1620 |
| gccggcacca | tgcaacttct | tcagcagcag | cagcaacagc | aacagcagca | gcagcagcag | 1680 |
| cagcagcagc | agcagcaaca | gcagcaggag | gtaatatccg | aaggcagcag | cagcgtgaga | 1740 |
| gcaagggagg | ccactgggc | tccctcttcc | tccaaggata | gttacctagg | gggcaattcg | 1800 |
| accatatctg | acagtgccaa | ggagttgtgt | aaagcagtgt | ctgtgtccat | ggggttgggt | 1860 |
| gtggaagcac | tggaacatct | gagtccaggg | agcagcttc | ggggcgactg | catgtacgcg | 1920 |
| tcgctcctgg | gaggtccacc | cgccgtgcgt | cccactcctt | gtgcgcctct | ggccgaatgc | 1980 |
| aaaggtcttt | ccctgacga | aggcccgggc | aaaggcactg | aagagactgc | tgagtattcc | 2040 |
| tctttcaagg | gaggttacgc | caaagggttg | gaaggtgaga | gtctgggctg | ctctggcagc | 2100 |

```
agtgaagcag gtagctctgg gacacttgag atcccgtcct cactgtctct gtataagtct    2160
ggagcagtag acgaggcagc agcataccag aatcgcgact actacaactt ccgctcgct     2220 ctgtccgggc cgccgcaccc cccgccccct acccatccac acgcccgcat caagctggag    2280
aacccgtcgg actacggcag cgcctgggct gcggcggcag cgcaatgccg ctatggggac    2340
ttggctagcc tacatggagg gagtgtagcc ggacccagca ctggatcgcc cccagccacc    2400
gcctcttctt cctggcatac tctcttcaca gctgaagaag gccaattata tgggccagga    2460
ggcgggggcg gcagcagtag cccaagcgat gctgggcctg tagcccccta tggctacact    2520
cggccccctc aggggctggc aagccaggag ggtgacttct ctgcctctga agtgtggtat    2580
cctggtggag ttgtgaacag agtcccctat cccagtccca gttgtgttaa aagtgaaatg    2640
ggaccttgga tggagaacta ctccggacct tatggggaca tgcgtttgga cagtaccagg    2700
gaccacgttt tacccatcga ctattacttc ccaccccaga agacctgcct gatctgtgga    2760
gatgaagctt ctggttgtca ctacggagct ctcacttgtg gcagctgcaa ggtcttcttc    2820
aaaagagctg cggaagggaa acagaagtat ctatgtgcca gcagaaatga ttgcaccatt    2880
gataaatttc ggaggaaaaa ttgtccatcg tgtcgtctcc ggaaatgtta tgaagcaggg    2940
atgactctgg gagctcgtaa gctgaagaaa cttggaaatc tcaaactaca ggaagaagga    3000
gaaaactcca gtgctggtag cccccactga gacccatccc agaagatgac tgtatcacac    3060
attgaaggct atgaatgtca acctatcttt cttaatgtcc tggaagccat tgagccagga    3120
gtggtgtgtg ccggacatga caacaaccag cctgattcct tgctgccctt gttatctagt    3180
ctcaacgagc ttggcgagag acagcttgta catgtggtca agtgggccaa ggccttgcct    3240
ggcttccgca acttgcatgt ggatgaccag atggcagtca ttcagtattc ctggatggga    3300
ctgatggtat ttgccatggg ttggcggtcc ttcactaatg tcaactctag gatgctctac    3360
tttgcacctg acctggtttt caatgagtat cgcatgcaca gtctcgaat gtacagccag    3420 tgcgtgagga tgaggcacct ttctcaagag tttggatggc tccagataac cccccaggaa    3480
ttcctgtgca tgaaagcact gctactcttc agcattattc cagtggatgg ctgaaaaat    3540 caaaaattct ttgatgaact tcgaatgaac tacatcaagg aacttgatcg catcattgca    3600
tgcaaaagaa aaaatcccac atcctgctca aggcgcttct accagctcac caagctcctg    3660
gattctgtgc agcctattgc aagagagctg catcaattca cttttgacct gctaatcaag    3720
tcccatatgg tgagcgtgga ctttcctgaa atgatggcag agatcatctc tgtgcaagtg    3780
cccaagatcc tttctgggaa agtcagccca tgtatttcca cacacagtga agatttggaa    3840
cctaataccc aaacccacct gttcccttt cagatgtctt ctgcctgtta tataactctg    3900
cactacttct ctggcatggg ccttggggga aattcctcta ctgatgtaca gtctgtcatg    3960
aacatgttcc ccaagttcta tttcctgggc ttttccttct ttcttttcct tcttctctgc    4020 ctctttacc ctcccatggc acattttgaa tccgctgcgt gttgtggctc ctgcctgtgt    4080
tttgagtttt gttgtatttc ttcaagtctg tgatgatctt cttgtggccc agtgtcaact    4140
gtgcttgttt atagcactgt gctgtgtgcc aaccaagcaa atgtttactc accttatgcc    4200
atggcaagtt tagagagcta taagtatctt gggaagaaac aaacagagag agtaaaaaaa    4260
ccaaaaaaaa aaaaaaaaa ccgaattc                                        4288
```

<210> SEQ ID NO 21
<211> LENGTH: 996
<212> TYPE: PRT
<213> ORGANISM: Rattus rattus

<400> SEQUENCE: 21

```
Met Glu Val Gln Leu Gly Leu Gly Arg Val Tyr Pro Arg Pro Pro Ser
1               5                   10                  15
Lys Thr Tyr Arg Gly Ala Phe Gln Asn Leu Phe Gln Ser Val Arg Glu
            20                  25                  30
Ala Ile Gln Asn Pro Gly Pro Arg His Pro Glu Ala Ala Ser Ile Ala
        35                  40                  45
Pro Pro Gly Ala Cys Leu Gln Gln Arg Gln Glu Thr Ser Pro Arg Arg
    50                  55                  60
Arg Arg Arg Gln Gln His Pro Glu Asp Gly Ser Pro Gln Ala His Ile
65                  70                  75                  80
Arg Gly Thr Thr Gly Tyr Leu Ala Leu Glu Glu Glu Gln Gln Pro Ser
                85                  90                  95
Gln Gln Gln Ser Ala Ser Glu Gly His Pro Glu Ser Gly Cys Leu Pro
            100                 105                 110
Glu Pro Gly Ala Ala Thr Ala Pro Gly Lys Gly Leu Pro Gln Gln Pro
        115                 120                 125
Pro Ala Pro Pro Asp Gln Asp Asp Ser Ala Ala Pro Ser Thr Leu Ser
    130                 135                 140
Leu Leu Gly Pro Thr Phe Pro Gly Leu Ser Ser Cys Ser Ala Asp Ile
145                 150                 155                 160
Lys Asp Ile Leu Ser Glu Ala Gly Thr Met Gln Leu Leu Gln Gln Gln
                165                 170                 175
Gln Gln Gln Gln Gln Gln Gln Gln Gln Gln Gln Gln Gln Gln Gln Gln
            180                 185                 190
Gln Gln Gln Glu Val Ile Ser Glu Gly Ser Ser Val Arg Ala Arg
        195                 200                 205
Glu Ala Thr Gly Ala Pro Ser Ser Ser Lys Asp Ser Tyr Leu Gly Gly
    210                 215                 220
Asn Ser Thr Ile Ser Asp Ser Ala Lys Glu Leu Cys Lys Ala Val Ser
225                 230                 235                 240
Val Ser Met Gly Leu Gly Val Glu Ala Leu Glu His Leu Ser Pro Gly
                245                 250                 255
Glu Gln Leu Arg Gly Asp Cys Met Tyr Ala Ser Leu Leu Gly Gly Pro
            260                 265                 270
Pro Ala Val Arg Pro Thr Pro Cys Ala Pro Leu Ala Glu Cys Lys Gly
        275                 280                 285
Leu Ser Leu Asp Glu Gly Pro Gly Lys Gly Thr Glu Glu Thr Ala Glu
    290                 295                 300
Tyr Ser Ser Phe Lys Gly Gly Tyr Ala Lys Gly Leu Glu Gly Glu Ser
305                 310                 315                 320
Leu Gly Cys Ser Gly Ser Ser Glu Ala Gly Ser Ser Gly Thr Leu Glu
                325                 330                 335
Ile Pro Ser Ser Leu Ser Leu Tyr Lys Ser Gly Ala Val Asp Glu Ala
            340                 345                 350
Ala Ala Tyr Gln Asn Arg Asp Tyr Tyr Asn Phe Pro Leu Ala Leu Ser
        355                 360                 365
Gly Pro Pro His Pro Pro Pro Thr His Pro His Ala Arg Ile Lys
    370                 375                 380
Leu Glu Asn Pro Ser Asp Tyr Gly Ser Ala Trp Ala Ala Ala Ala
385                 390                 395                 400
Gln Cys Arg Tyr Gly Asp Leu Ala Ser Leu His Gly Gly Ser Val Ala
```

-continued

```
                405                 410                 415
Gly Pro Ser Thr Gly Ser Pro Ala Thr Ala Ser Ser Trp His
            420                 425                 430
Thr Leu Phe Thr Ala Glu Glu Gly Gln Leu Tyr Gly Pro Gly Gly
            435                 440                 445
Gly Gly Ser Ser Pro Ser Asp Ala Gly Pro Val Ala Pro Tyr Gly
            450                 455                 460
Tyr Thr Arg Pro Pro Gln Gly Leu Ala Ser Gln Glu Gly Asp Phe Ser
465                 470                 475                 480
Ala Ser Glu Val Trp Tyr Pro Gly Gly Val Val Asn Arg Val Pro Tyr
                485                 490                 495
Pro Ser Pro Ser Cys Val Lys Ser Glu Met Gly Pro Trp Met Glu Asn
            500                 505                 510
Tyr Ser Gly Pro Tyr Gly Asp Met Arg Leu Asp Ser Thr Arg Asp His
            515                 520                 525
Val Leu Pro Ile Asp Tyr Tyr Phe Pro Pro Gln Lys Thr Cys Leu Ile
    530                 535                 540
Cys Gly Asp Glu Ala Ser Gly Cys His Tyr Gly Ala Leu Thr Cys Gly
545                 550                 555                 560
Ser Cys Lys Val Phe Phe Lys Arg Ala Ala Glu Gly Lys Gln Lys Tyr
                565                 570                 575
Leu Cys Ala Ser Arg Asn Asp Cys Thr Ile Asp Lys Phe Arg Arg Lys
            580                 585                 590
Asn Cys Pro Ser Cys Arg Leu Arg Lys Cys Tyr Glu Ala Gly Met Thr
            595                 600                 605
Leu Gly Ala Arg Lys Leu Lys Lys Leu Gly Asn Leu Lys Leu Gln Glu
    610                 615                 620
Glu Gly Glu Asn Ser Ser Ala Gly Ser Pro Thr Glu Asp Pro Ser Gln
625                 630                 635                 640
Lys Met Thr Val Ser His Ile Glu Gly Tyr Glu Cys Gln Pro Ile Phe
                645                 650                 655
Leu Asn Val Leu Glu Ala Ile Glu Pro Gly Val Val Cys Ala Gly His
            660                 665                 670
Asp Asn Asn Gln Pro Asp Ser Phe Ala Ala Leu Leu Ser Ser Leu Asn
            675                 680                 685
Glu Leu Gly Glu Arg Gln Leu Val His Val Val Lys Trp Ala Lys Ala
    690                 695                 700
Leu Pro Gly Phe Arg Asn Leu His Val Asp Asp Gln Met Ala Val Ile
705                 710                 715                 720
Gln Tyr Ser Trp Met Gly Leu Met Val Phe Ala Met Gly Trp Arg Ser
                725                 730                 735
Phe Thr Asn Val Asn Ser Arg Met Leu Tyr Phe Ala Pro Asp Leu Val
            740                 745                 750
Phe Asn Glu Tyr Arg Met His Lys Ser Arg Met Tyr Ser Gln Cys Val
            755                 760                 765
Arg Met Arg His Leu Ser Gln Glu Phe Gly Trp Leu Gln Ile Thr Pro
    770                 775                 780
Gln Glu Phe Leu Cys Met Lys Ala Leu Leu Leu Phe Ser Ile Ile Pro
785                 790                 795                 800
Val Asp Gly Leu Lys Asn Gln Lys Phe Phe Asp Glu Leu Arg Met Asn
                805                 810                 815
Tyr Ile Lys Glu Leu Asp Arg Ile Ile Ala Cys Lys Arg Lys Asn Pro
            820                 825                 830
```

-continued

```
Thr Ser Cys Ser Arg Arg Phe Tyr Gln Leu Thr Lys Leu Leu Asp Ser
        835                 840                 845

Val Gln Pro Ile Ala Arg Glu Leu His Gln Phe Thr Phe Asp Leu Leu
    850                 855                 860

Ile Lys Ser His Met Val Ser Val Asp Phe Pro Glu Met Met Ala Glu
865                 870                 875                 880

Ile Ile Ser Val Gln Val Pro Lys Ile Leu Ser Gly Lys Val Ser Pro
                885                 890                 895

Cys Ile Ser Thr His Ser Glu Asp Leu Glu Pro Asn Thr Gln Thr His
            900                 905                 910

Leu Phe Pro Phe Gln Met Ser Ser Ala Cys Tyr Ile Thr Leu His Tyr
        915                 920                 925

Phe Ser Gly Met Gly Leu Gly Gly Asn Ser Ser Thr Asp Val Gln Ser
        930                 935                 940

Val Met Asn Met Phe Pro Lys Phe Tyr Phe Leu Gly Phe Ser Phe Phe
945                 950                 955                 960

Leu Phe Leu Leu Leu Cys Leu Phe Tyr Pro Pro Met Ala His Phe Glu
                965                 970                 975

Ser Ala Ala Cys Cys Gly Ser Cys Leu Cys Phe Glu Phe Cys Cys Ile
            980                 985                 990

Ser Ser Ser Leu
        995
```

<210> SEQ ID NO 22
<211> LENGTH: 12
<212> TYPE: DNA
<213> ORGANISM: Artificial Sequence
<220> FEATURE:
<223> OTHER INFORMATION: Hypothetical Oligonucleotide.

<400> SEQUENCE: 22
gctggttgta ag                                                         12

<210> SEQ ID NO 23
<211> LENGTH: 4
<212> TYPE: PRT
<213> ORGANISM: Artificial Sequence
<220> FEATURE:
<223> OTHER INFORMATION: Hypothetical Peptide.

<400> SEQUENCE: 23

Ala Gly Cys Lys
1

<210> SEQ ID NO 24
<211> LENGTH: 32
<212> TYPE: DNA
<213> ORGANISM: Artificial Sequence
<220> FEATURE:
<223> OTHER INFORMATION: Synthetic Oligonucleotide Probe A.

<400> SEQUENCE: 24
cttttgaaga agaccttaca gccctcacag gt                                   32

<210> SEQ ID NO 25
<211> LENGTH: 38
<212> TYPE: DNA
<213> ORGANISM: Artificial Sequence
<220> FEATURE:
<223> OTHER INFORMATION: Synthetic Oligonucleotide Probe B.

```
<400> SEQUENCE: 25
ggaccatgtt ttgcccattg actattactt tccacccc                              38

<210> SEQ ID NO 26
<211> LENGTH: 15
<212> TYPE: PRT
<213> ORGANISM: Artificial Sequence
<220> FEATURE:
<223> OTHER INFORMATION: Synthetic Peptide.

<400> SEQUENCE: 26

Asp His Val Leu Pro Ile Asp Tyr Tyr Phe Pro Pro Gln Lys Thr
1               5                   10                  15
```

ANDROGEN RECEPTOR PROTEINS, RECOMBINANT DNA MOLECULES CODING FOR SUCH, AND USE OF SUCH COMPOSITIONS

RELATED APPLICATIONS

This application is a divisional of U.S. application Ser. No. 07/182,646, filed on Apr. 15, 1988, which is hereby incorporated by reference in its entirety.

This invention was made in the course of research supported in part by grants from the National Institutes of Health (NIH HD 16910, HD 04466, and HD 18968).

TECHNICAL FIELD OF THE INVENTION

This invention relates to recombinant DNA molecules and their expression products. More specifically this invention relates to recombinant DNA molecules coding for androgen receptor protein, androgen receptor protein, and use of the DNA molecules and protein in investigatory, diagnostic and therapeutic applications.

BACKGROUND OF THE INVENTION

The naturally occurring androgenic hormones, testosterone and its 5 α-reduced metabolite, dihydrotestosterone, are synthesized by the Leydig cells of the testes and circulate throughout the body where they diffuse into cells and bind to the androgen receptor protein ("AR"). Androgens, acting through their receptor, stimulate development of the male genitalia and accessory sex glands in the fetus, virilization and growth in the pubertal male, and maintenance of male virility and reproductive function in the adult. The androgen receptor, together with other steroid hormone receptors constitute a family of trans-acting transcriptional regulatory proteins that control gene transcription through interactions with specific gene sequences.

When prostate cancer is found to be confined to the prostate gland, the treatment of choice is surgical removal. However, 50 to 80% of prostate cancer patients already have metastases at the time of diagnosis. Most of their tumors (70 to 80%) respond to the removal of androgen by castration or by suppression of luteinizing hormone secretion by the pituitary gland using a gonadotropin releasing hormone analogue alone or in combination with an anti-androgen. The degree and duration of response to this treatment is highly variable (10% live <6 months, 50% live <3 years, and 10% live >10 years.) Initially cancer cells regress without androgen stimulation, but ultimately the growth of androgen independent tumor cells continues (3b). At present it is not possible to predict on an individual basis which patient will respond to hormonal therapy and for how long. If poorly responsive patients could be identified early, they could be treated by alternative forms of therapy (e.g. chemotherapy) at an earlier stage when they might be more likely to respond.

Studies on androgen receptors in prostate cancer have suggested that a positive correlation may exist between the presence of androgen receptors in cancer cells and their dependence on androgenic hormone stimulation for growth. (An analogous situation exists in mammary carcinoma where there is a correlation between estrogen receptors and regression of the tumor in response to estrogen withdrawal). However, methodological problems in the measurement of androgen receptors have prevented the routine use of androgen receptor assays in the diagnostic evaluation of prostate cancer. Prior to our preparation of androgen receptor antibodies, all androgen receptor assays were based on the binding of [$^3$H]-labeled androgen. These assays have been unreliable in human prostate cancer tissue because of the extreme lability of the androgen binding site and the presence of unlabeled androgen in the tissue. Endogenous androgen occupies the binding site on the receptor and dissociates very slowly (t ½24–48 hr at OC). A further problem is that biopsy samples are quite small, making it difficult to obtain sufficient tissue for [$^3$H]-androgen binding assays. Moreover, prostate cancer is heteroyenous with respect to cell types. Thus within a single biopsy sample there is likely to be an uneven distribution of cells containing androgen receptors.

Development of the male phenotype and maturation of male reproductive function are dependent on the interaction of androgenic hormones with the androgen receptor protein and the subsequent function of the receptor as a trans-actiny inducer of gene expression. It has become well established over the past twenty-five years that genetic defects of the androgen receptor result in a broad spectrum of developmental and functional abnormalities ranging from genetic males (46, XY) with female phenotype to phenotypically normal males with infertility. Isolation of the structural gene for the androgen receptor makes it possible to define the nature of these genomic defects in molecular terms. Analysis of the functional correlates of the genetic defects may lead to a better understanding of the regulation of androgen receptor gene expression and of the mechanism of androgen action in male sexual development and function.

The androgen insensitivity syndrome, known also as testicular feminization, is characterized by an inability to respond to androgen due to a defect in the androgen receptor, the protein that mediates the action of androgen within the cell. Androgen insensitivity is an inherited X-linked trait that occurs in both complete and incomplete forms. The complete form results in failure of male sex differentiation during embryogenesis and absence of virilization at puberty. The result is a 46, XY genetic male with testes and male internal ducts. The testes produce normal amounts of testosterone and Mullerian inhibiting substance. Consequently development of the uterus is inhibited as in the normal male. Because of the inability to respond to androgen, the external genitalia remain in the female phenotype with normal clitoris and labia. A small vagina develops from the urogenital sinus and ends in a blind pouch. At puberty feminization with breast development and female contours occur in response to testicular estrogen, however, there is no growth of sexual hair even though circulating testosterone concentrations are equal to or greater than levels in the normal male.

Incomplete forms of the androgen insensitivity syndrome include a spectrum of phenotypes resulting from varying degrees of incomplete androgen responsiveness. At one extreme, individuals have mild enlargement of the clitoris and sparse pubic hair. The opposite extreme is characterized by more complete masculinization with varying degrees of hypospadias deformity but predominantly a male phenotype. It has been reported that some adult men with severe oligospermia or azoospermia who are otherwise normal, have defects in the androgen receptor. These may include as many as 10% of infertile males.

The genetic defect eliciting this range of abnormalities is thought to be a single biochemical event at the level of the gene for the androgen receptor. The androgen receptor is a high affinity androgen binding protein that mediates the effects of testosterone and dihydrotestosterone by functioning as a trans-acting inducer of gene expression. For proper male sexual development to occur, there is a requirement for androgen and its receptor at a critical time during embryogenesis and during puberty. The majority of individuals with the androgen insensitivity syndrome have a history of affected family members, although about a third are thought to represent new mutations of this X-linked disorder. The incidence ranges from 1 in 20, 000 to 60,000 male births.

In studies of families with clinical evidence of the androgen insensitivity syndrome, four main categories were recognized that range from the most severe, complete absence of receptor binding activity in a genetic male with female phenotype, to qualitatively normal receptor in affected individuals. Second in severity are affected individuals with qualitatively abnormal androgen binding by receptor present in normal levels. Examples include the failure of sodium molybdate (a reagent often used in studies on steroid receptors) to stabilize the receptor of affected individuals when molybdate is known to stabilize the wild-type receptor. Lability of the receptor under conditions that normally cause transformation has also been reported. A third group expresses a decreased amount of receptor with wild-type in vitro binding characteristics. The final grouping contains those androgen insensitivity patients in whom no abnormality in receptor is detected. In a recent study of this form of the syndrome, the androgen receptor was as capable of binding oligonucleotides as the wild-type receptor. Indeed, with the techniques available until only recently, it has been difficult in certain cases to document an androgen receptor defect in affected individuals.

Experimental methods used in assessing receptor defects in the past have relied on the ability of receptor to bind androgen with high affinity. The limitation of this methodology is that it is not possible to distinguish between the lack of expression of the receptor and loss of androgen binding activity. An example of how inadequate methodology complicates diagnosis is the absence of detectable receptor binding activity in patients who are partially virilized. It is theoretically possible for a mutation to occur which allows the receptor with defective androgen binding activity to induce gene transcription. Biologically active truncated forms of the glucocorticoid receptor that lack steroid binding activity but retain the DNA binding domain have been demonstrated using genetically engineered mutants.

Purification of the androgen receptor has been difficult to accomplish due to its low concentration and high degree of instability. Reported attempts at purification using either conventional methods of column chromatography or steroid-affinity chromatography have yielded insufficient amounts of receptor protein to allow even the preparation of monoclonal antibodies.

An early report on the partial purification of the androgen receptor was disclosed by Mainwaring et al. in "The use of DNA—cellulose chromatography and isoelectric focusing for the characterization and partial purification of steroid-receptor complexes." Biochem J, 134, 113–127 (1973). They used DNA-cellulose chromatography and isoelectric focusing to isolate the receptor from rat ventral prostate and determined its physiochemical properties. This group was among the first to attempt the use of steroid affinity chromatography in conjunction with conventional chromatography, using the affinity label 17B-bromoacetoxytestosterone in receptor purification (See Mainwaring et al., "Use of the affinity label 17B-bromoacetoxytestosterone in the purification of androgen receptor proteins," Perspectives in Steroid Receptor Research, (1980)). Partial purification of androgen receptor has also been attempted from other tissue sources, such as ram seminal vesicles (See Foekens et al., Molecular Cellular Endocr, 23, 173–186 (1981) and Foekens et al., "Purification of the androgen receptor of sheep seminal vesicles;" Biochem Biophys Res Comm, 104, 1279–1286 (1982)). The partially purified receptor displayed characteristics of a proteolyzed receptor, but a purification of 2,000 fold was reported with a recovery of 33% (See Foekens et al., "Purification of the androgen receptor of sheep seminal vesicles," Biochem Biophys Res Comm, 104, 1279–1286 (1982)). Later attempts at purification continued to combine steroid affinity chromatography with conventional techniques, reportedly achieving significant purification, but recoveries too low for further analysis (See Chany et al., "Purification and characterization of androgen receptor from steer semenal vesicle," Biochemistry 21, 4102–4109 (1982), Chany et al., "Purification and characterization of the androgen receptor from rat ventral prostate," Biochemistry 22, 6170–6175 (1983) and Chang et al., "Affinity labeling of the androgen receptor in rat prostate cytosol with 17B-[(bromoacetyl)oxy]-5-alpha-androstan-3-one," Biochemistry 23, 2527–2533 (1984)). More recent studies examine the effectiveness of a variety of immobilized androgens for their ability to bind the androgen receptor (See De Larminat et al., "Synthesis and evaluation of immobilized androgens for affinity chromatography in the purification of nuclear androgen receptor," The Prostate 5, 123–140 (1984) and Bruchovsky et al, "Chemical demonstration of nuclear androgen receptor following affinity chromatography with immobilized ligands," The Prostate 10, 207–222 (1987)). Despite these efforts, the receptor has not been purified to homogeneity and the quantities of purified androgen receptor obtained have been insufficient for the production of antisera.

Clinical assays for the androgen receptor now include several methods. The most common is the binding of tritium-labeled hormone and measurement of binding using a charcoal adsorption assay. Either a natural androgen, such as dihydrotestosterone, or synthetic androgen, such as mibolerone or methyltrienolone (R1881), can be used. An advantage of the latter in human tissue is that it is not significantly metabolized and does not bind to the serum androgen binding protein, sex steroid binding globulin. A limitation of radioisotope labeling of receptor is interference caused by endogenous androgen. Although exchange assays for the androgen receptor have been described (See Carroll et al., J Steroid Biochem 21, 353–359 (1984) and Traish et al., J Steroid Biochem 23, 405–413 (1985)), their effectiveness is limited by the slow kinetics of dissociation of the endogenous receptor-bound androgen.

Another method used to assess receptor status is autoradiography. In this method disclosed in Barrack et al., "Current concepts and approaches to the study of prostate cancer," Progress in Clinical and Biological Research, 239, 155–187 (1987) the radioactively labeled androgen is incubated with slide-mounted tissue sections of small tissue biopsy specimens which are then frozen, sectioned and fixed. Nuclear localization of radioactivity is detected by exposure of tissue sections to x-ray film. This technique requires considerable technical expertise, is labor intensive, and requires extended periods of exposure time. It is therefore of limited usefulness in general clinical assays. Another problem is high levels of background signal, i.e. a high noise/signal ratio, making it difficult to distinguish receptor-bound nuclear radioactivity from unbound radioactivity distributed throughout the cells.

WO 87/05049 (Shine) discloses a method for the production of purified steroid receptor proteins, specifically estrogen receptor proteins, through the expression of recombinant DNA encoding for such proteins in eukaryotic host cells. However, the reference does not disclose the sequence for androgen receptor protein, nor does it disclose a method for obtaining such a sequence.

SUMMARY OF THE INVENTION

The present invention provides a DNA sequence characterized by a structural gene coding for a polypeptide having substantially the same biological activity as androgen receptor protein. A DNA sequence encoding androgen receptor protein or a protein having substantially the same biological activity as androgen receptor activity is also provided. DNA sequences may be obtained from cDNA or genomic DNA, or prepared using DNA synthesis techniques.

The invention further discloses cloning vehicles comprising a DNA sequence comprising a structural gene encoding a polypeptide having substantially the same biological activity as androgen receptor protein. Cloning vehicles comprising a DNA sequence encoding androgen receptor protein or a protein having substantially the same biological activity as androgen receptor protein is also provided. The cloning vehicles further comprise a promoter sequence upstream of and operatively linked to the DNA sequence. In general the cloning vehicles will also contain a selectable marker, and, depending on the host cell used, may contain such elements as regulatory sequences, polyadenylatlon signals, enhancers and RNA splice sites.

The invention further provides cells transfected or transformed to produce androgen receptor protein or a protein having substantially the same biological activity as androgen receptor protein.

A further aspect of the invention provides a purified androgen receptor protein and purified polypeptides and proteins have substantially the same biological activity as androgen receptor protein, and methods for producing such proteins and polypeptides.

BRIEF DESCRIPTION OF THE DRAWINGS

FIG. 1 shows a comparison of DNA-binding domains of the human androgen receptor (hAR) with members of the nuclear receptor family. (A) is a comparison of oligo A nucleotide sequence (SEQ ID NO:1) with sequences of hAR (SEQ ID NO:2) and other nuclear receptors: hPR, human progesterone receptor (SEQ ID NO:3); hMR, human mineralocorticoid receptor (SEQ ID NO:4); hGR, human glucocorticoid receptor (SEQ ID NO:5); hER, human estrogen receptor (SEQ ID NO:6); hT3R, human thyroid hormone receptor (SEQ ID NO:7); hRAR, human retinoic acid receptor (SEQ ID NO:8). Chromosomal locations are shown in parentheses at the left. Nucleotide identity between oligo A and hAR is indicated with an asterisk The percent homology with oligo A Is In parentheses at the right of each sequence. (B) shows the structure of fibroblast clone ARHFL1 human fibroblast clone [1]. Nucleotide residues are numbered from the 5'-terminus. Restriction endonuclease sites were determined by mapping or were deduced from DNA sequence. The TGA translation termination codon, determined by comparison with hPR, hMR and hGR, follows a long open reading frame containing sequences homologous to those of other steroid receptors. Arrows indicate exon boundaries in genomic clone X05AR. The hatched area is the putative DNA-binding domain. (C) shows a comparison of amino acid sequences of the AR DNA-binding domain (SEQ ID NO:9) with sequences of the nuclear receptor family. AR amino acid sequence was deduced from nucleotide sequence of clone ARHFL1 and is numbered beginning with the first conserved cysteine residue (+). Amino acid numbers in parentheses at the left indicate the residue number of the first conserved cysteine from the references indicated below. Percent homology with hAR is indicated in parentheses on the right. The region of the DNA-binding domain from which the oligo A sequence was derived is underlined in hAR. Coding DNA of residues 1 to 31 is contained within genomic clone X05AR. Abbreviations are hPR, human progesterone receptor (SEQ ID NO:10); hMR, human mineralocorticoid receptor (SEQ ID NO:11); hGR, human glucocorticoid receptor (SEQ ID NO:12); hER, human estrogen receptor (SEQ ID NO:13); cVDR, chicken vitamin D receptor (SEQ ID NO:14); hT3R, human thyroid hormone receptor (SEQ ID NO:15); vERBA, erb A protein from avian erythroblastosis virus (SEQ ID NO:16); and hRAR, human retinoic acid receptor (SEQ ID NO:17). Abbreviations for amino acid residues are: A, Ala; C, Cys; D, Asp; E, Glu; F, Phe; G, Gly; H, His; I, Ile; K, Lys; L, Leu; M, Met, N, Asn; P, Pro; Q, Gln; R, Arg; S, Ser, T, Thr, V, Val; W, Trp; and Y, Tyr.

FIG. 2 illustrates the steroid binding properties of expressed AR cDNA. (A) shows the structure of pCMVAR in the expression vector pCMV containing the human cytomegalovirus (CMV) promoter of the immediate early gene, poly(A) addition-transcription terminator region of the human growth hormone gene (hGH poly A), SV40 origin of replication (SV40 Ori), and a polylinker region for insertion of cDNAs. The plasmid pTEBR contains the ampicillin resistance gene (Amp). (B) shows saturation analysis of [$^3$H]dihydrotestosterone binding in extracts of PCMVAR transfection of COS M6 cells. Portions of cylosol (0.1 ml, 0.3 mg/ml protein) were incubated overnight at 4° C. with increasing concentrations of $^3$H-labeled hormone and analyzed by charcoal adsorption. Nonspecific binding increased from 18% to 37% of total bound radioactivity. (C) shows a Scatchard plot analysis of [$^3$H]dihydrotestosterone binding. Error estimation was based on linear regression analysis (r=0.966). (D) illustrates the competition of unlabeled steroids for binding of 5 nM [$^3$H]dihydrotestosterone in transfected COS M6 cell extracts. Unlabeled steroids were added at 10- and 100-fold excess of labeled hormone. Specific binding was determined as previously described.

FIGS. 4A–I shows the doublstranded DNA sequence (SEQ ID NO:18) encoding the human androgen receptor protein.

FIGS. 5A–E shows the complete single-stranded DNA sequence (5082 bases) of the human androgen receptor (SEQ ID NO:18) and the deduced amino acid sequence (SEQ ID NO:19). No intron sequence is included.

FIGS. 6A–6D shows the complete single-stranded DNA sequence (4260 bases) of the rat androgen receptor (SEQ ID NO:20) and the deduced amino acid sequence (SEQ ID NO:21).

DETAILED DESCRIPTION OF THE INVENTION

Figure 3:
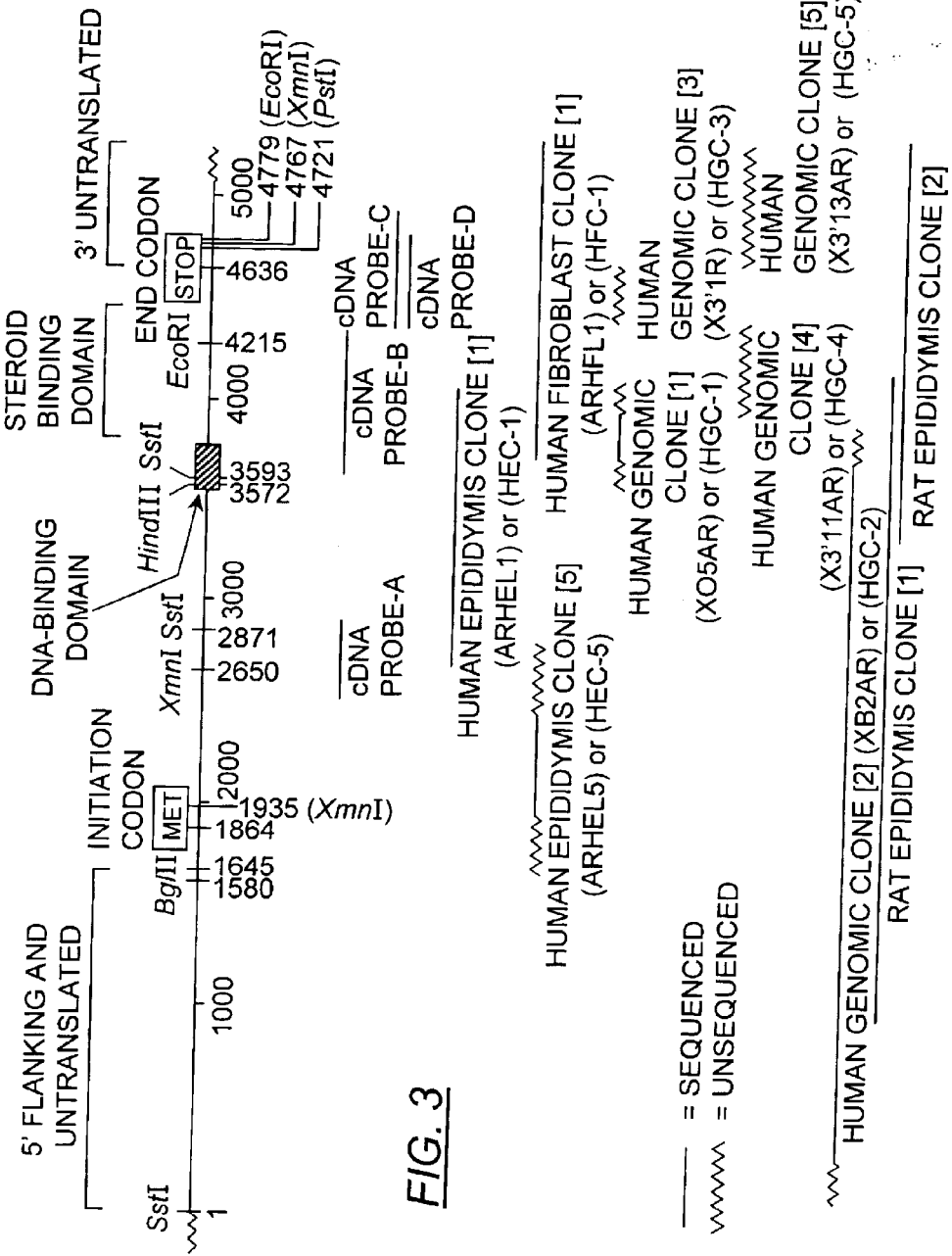
FIG. 3 is compiled clone map of the human androgen receptor. The ma shows the structure of the human androgen receptor gene and the relative positions of the nucleic acid sequences contain d in the cDNA probes [A], [B], [C] and [D], human fibroblast clone [1], human epididymis clones [1] and [5], human genomic clones [1], [3], [4] and [5], and rat epididymis clones [1] and [2].

In the Description the Following Terms are Employed

Nucleotide

A monomeric unit of DNA or RNA consisting of a sugar moiety (pentose), a phosphate, and a nitrogenous heterocyclic base. The base is linked to the sugar moiety via the glycosidic carbon (1'carbon of the pentose) and that combination of base and sugar is a nucleoside. The base characterizes the nucleotide. The four DNA bases are adenine ("A"), guanine ("G"), cytosine ("C") and thymine ("T"). The four RNA bases are A, G, C and uracil ("U"). A and G are purines, abbreviated to R, and C, T, and U are pyrimidines, abbreviated to Y.

DNA Sequence

A linear series of nucleotides connected one to the other by phosphodiester bonds between the 3' and 5' carbons of adjacent pentoses.

Codon

A DNA sequence of three nucleotides (a triplet) which encodes through mRNA an amino acid, a translational start signal or a translational termination signal. For example, the nucleotide triplets TTA, TTG, CTT, CTC, CTA and CTG encode for the amino acid leucine ("Leu"), TAG, TAA and TGA are translational stop signals and ATG is a translational start signal.

Reading Frame

The grouping of codons during translation of mRNA into amino acid sequences. During translation the proper reading frame must be maintained. For example, the sequence GCTGGTTGTMG (SEQ ID NO:22) may be translated in three reading frames or phases, each of which affords a different amino acid sequence:

GCT GGT TGT MG-Ala-Gly-Cys-Lys (SEQ ID NO:23)

G CTG GTT GTA AG-Leu-Val-Val

GC TGG TTG TM A-Trp-Leu-(Stop)

Polypeptide

A linear series of amino acids connected one to the other by peptide bonds between the α-amino and carboxy groups of adjacent amino acids.

Genome

The entire DNA of a substance. It includes inter alia the structural genes encoding for the polypeptides of the substance, as well as operator, promoter and ribosome binding and interaction sequences including sequences such as the Shine-Dalgarno sequences.

Structural Gene

A DNA sequence which encodes through its template or messenger RNA ("mRNA") a sequence of amino acids characteristic of a specific polypeptide.

Transcription

The process of producing mRNA from a structural gene.

Translation

The process of producing a polypeptie from mRNA.

Expression

The process undergone by a structural gene to produce a polypeptide. It is a combination of transcription and translation.

Plasmid

A non-chromosomal double-stranded DNA sequence comprising an intact "replicon" such that the plasmid is replicated in a host cell. When the plasmid is placed within a unicellular organism, the characteristics of that organism are changed or transformed as a result of the DNA of the plasmid. For example, a plasmid carrying the gene for tetracycline resistance ($Tet^R$) transforms a cell previously sensitive to tetracycline into one which is resistant to it. A cell transformed by a plasmid is called a "transformant".

Phage or Bacteriophage

Bacterial virus many of which include DNA sequences encapsidated in a protein envelope or coat ("capsid"). In a unicellular organism a phage may be introduced as free DNA by a process called transfection.

Cloning Vehicle

A plasmid, phage DNA or other DNA sequences which are able to replicate in a host cell, characterized by one or a small number of endonuclease recognition sites at which such DNA sequences may be cut in a determinable fashion without attendant loss of an essential biological function of the DNA, e.g., replication, production of coat proteins or loss of promoter or binding sites, and which contain a marker suitable for use in the identification of transformed cells, e.g., tetracycline resistance or ampicillin resistance. A cloning vehicle is often called a vector.

Cloning

The selection and propagation of a single species.

Recombinant DNA Molecule

A hybrid DNA sequence comprising at least two nucleotide sequences, the first sequence not normally being found together in nature with the second.

Expression Control Sequence

A DNA sequence of nucleotices that controls and regulates expression of structural genes when operatively linked to those genes.

To attain the objects of this invention it was necessary to determine the amino acid sequence and the DNA sequence of the structural gene encoding androgen receptor protein. One conventional approach would involve starting with the purified androgen receptor protein. However, as described above, significant amounts of the protein for such purposes have not been obtained.

An alternative approach to circumvent the overwhelming difficulty of androgen receptor protein purification is direct isolation of the DNA encoding the messenger RNA for androgen receptor protein.

Our strategy for isolating AR DNA was based on evidence that the AR gene is X-linked and that no other steroid receptor gene is located on the X chromosome. Sequence data are available from cDNAs for glucocorticoid, estrogen, progesterone, mineralocorticoid and vitamin D receptors. Comparison of the derived amino acid sequences has revealed a central region of high cysteine content which was found also in the v-erb A oncoyene product recently identified as the thyroid hormone receptor. Within this 61–63 amino acid region is an arrangement of 9 cysteine residues that are absolutely conserved among steroid receptors thus far characterized. The overall homology among sequences in this conserved region ranges between 40 and 90%. We assumed that AR would resemble other members of the steroid receptor family in the conserved DNA-binding domain.

A human X chromosomal library was screened with the synthetic oligonudeotide probe A (Oligo A sequence=$5'$ CTT TTG MG MG ACC TTA CAG CCC TCA CAG GT $3'$; SEQ ID NO:24) of FIG. 1(A) designed as a consensus sequence from the conserved sequence of the DNA-binding domain of other steroid receptors. Screening the library with the oligo A probe resulted in several recombinants whose inserts were cloned into bacteriophage M13 DNA and sequenced. One recombinant clone (Charon 35 X05AR) (human genomic clone [1]) contained a sequence similar to, yet distinct from, the DNA-binding domains of other steroid receptors. It had 84% sequence identity with oligo A, while other receptor DNAs were 78% to 91% homologous with consensus oligonucleotide.

From the nucleotide sequence just 5' of the DNA-binding domain, oligonucleotide probe B (Oligonucleotide B sequence=5' GGA CCA TGT UT GCC CAT TGA CTA TTA CTT TCC ACC CC 3'; SEQ ID NO:25) was synthesized and used to screen bacteriophage lambda gt11 cDNA libraries from human epididymis and cultured human foreskin fibroblasts. Recombinant phage (unamplified) screened with this oligonucleotide by in situ hybridization revealed one positive clone in each library. The epididymal clone (gt11 ARHEL1) (human epididymis clone [1]) contained the complete DNA-binding domain and approximately 1.5 kb of upstream sequence, whereas the fibroblast clone (gt11 ARHFL1) (human fibroblast clone [1]) shown in FIG. 1(B) contained the DNA-binding domain and 1.5 kb of downstream sequence. The DNA-binding domains of the cDNA isolates were identical to that of the genomic exon sequence.

Transient expression in monkey kidney cells (COS M6) demonstrated that the human foreskin fibroblast cDNA fragment encodes the steroid-binding domain of hAR. A DNA fragment (ARHFLIH-X) extending 5' to 3' from the Hind III site within the putative DNA-binding domain through the stop codon (TGA) was cloned into pCMV as shown in FIG. 2(A). Expression was facilitated by adding to the 5' end a consensus translation initiation sequence containing the methionine codon (ATG) in reading frame. Transfection of the recombinant construct produced a protein with high-affinity for [$^3$H]dihydrotestosterone, FIG. 2(C) saturable at physiological levels of hormone. See FIG. 2(B). The binding constant [$K_d$=2.7 (+1.4)×10$^{-10}$M] was nearly identical to that of native AR. The level of expressed protein, 1.3 pmol per milligram of protein, was 20 to 60 times greater than that in male reproductive tissues. Mock transfections without plasmid or transfections with plasmid DNA lacking th AR insert yielded no specific binding of dihydrotestosterone. FIG. 2(D) shows steroid specificity was identical to that of native AR, with highest affinity for dihydrotestosterone and testosterone, intermediate affinity for progesterone and estradiol, and low affinity for cortisol.

FIG. 3 is a clone map compiled to show the human androgen receptor gene and the nucleic acid sequences in the cDNA clones, human genomic clones, human fibroblast clones, human epididymis clones, and rat epididymis clones. Human fibroblast clone [1] extended through the stop codon or the C-terminal end of the androgen receptor protein. To isolate and elucidate the sequence of the 5' or N-terminal end of the androgen receptor protein, we used a EcoRl/Sstl fragment (EcoRl site was from the linker) from the 5' end of humanepididymis clone [1] as a probe (cDNA probe [A]), to rescreen the human X chromosomal library by standard techniques. By these techniques, human genomic clone [2] was isolated and in turn used as a probe to rescreen a human epididymis library and isolate human epididymis clone (5]. The N-terminal sequence was elucidated along with the 5' flanking sequence of the androgen receptor protein and gene. Human genomic clones [3], [4] and [5] for the sequence 3' of human genomic clone [1] were obtained using cDNA probes B [a Hind III/EcoRl fragment] and C [an EcoRl fragment], by screening and isolating by standard techniques.

Two rat clones, rat epididymis clones [1] and [2], were isolated from a rat epididymis cDNA library using as probes the complete human epididymis clone [1] and a EcoRl/Pstl fragment, cDNA probe [D], respectively. These rat clones contained the entire protein coding sequence for the rat androgen receptor, plus flanking 5' and 3' untranslated sequences which were used to confirm the sequence of the human androgen receptor.

The complete double-stranded sequence (SEQ ID NO:18) encoding the human androgen receptor protein was determined and is set forth in FIG. 4. The single-stranded DNA sequence (SEQ ID NO:18) encoding human androgen receptor protein along with the amino acid sequence (SEQ ID NO:19) which it codes for are set forth in FIG. 5. The single stranded DNA sequence (SEQ ID NO:20) and the amino acid sequence (SEQ ID NO:21) for the rat androgen receptor protein is set forth in FIG. 6.

Recombinant DNA human fibroblast clone [1] isolated from human foreskin fibroblast cDNA gt11 expression library, human epididymis clones [1] and [5] isolated from human epididymis cDNA gt11 expression library were deposited in the American Type Culture Collection with accession numbers ATCC # 40439, ATCC # 40442 and ATCC # 40440, respectively. Human genomic clones [1], [2], [3], [4] and [5] which were isolated from human X chromosome lambda Charon 35 library available as ATCC # 57750 have been deposited with the American Type Culture Collection with accession numbers ATCC # 40441, ATCC # 40443, ATCC # 40444, ATCC # 40445 and ATCC # 40446, respectively.

A wide variety of hostconing vehicle combinations may be usefully employed in cloning the double-stranded DNA disclosed herein. For example, useful cloning vehicles may include chromosomal, non-chromosomal and synthetic DNA sequences such as various known bacterial plasmids and wider host range plasmids such as pCMV and vectors derived from combinations of plasmids and phase DNA such as plasmids which have been modified to employ phage DNA expression control sequences. Useful hosts may include bacterial hosts, yeasts and other fungi, animal or plant hosts, such as Chinese Hamster Ovary Cells (CHO), or monkey kidney cells (COS M6), and other hosts. The particular selection of host-cloning vehicle combinations may be made by those of skill in the art after due consideration of factors such as the source of the DNA- i.e. genomic or cDNA.

Cloning vehicles for usein carrying out the present invention will further comprise a promoter operably linked to the DNA sequence encoding the androgen receptor protein. In some instances it is preferred that cloning vehicles further comprise an origin of replication , as well as sequences which regulate and/or enhance expression levels, depending on the host cell selected.

Techniques for transforming hosts and expressing foreign cloned DNA in them are well known in the art (See, for example, Maniatis et al., infra). Cloning vehides used for expressing foreign genes in bacterial hosts will generally contain a selectable marker, such as a gene for antibiotic resistance, and a promoter which functions in the host cell.

Eukaryotic microorganisms, such as the yeast Saccharomyces cerevisiae, may also be used as host cells. Cloning vehicles will generally comprise a selectable marker, such as the nutritional marker TRP, which allows selection in a host strain carrying a trpt mutation. To facilitate purification ot an anoroyen receptor protein produced in a yeast transformant, a yeast gene encoding a secreted protein may be joined to the sequence encoding androgen receptor protein.

Higher eukaryotic cells can also serve as host cells in carrying out the present invention. Cultured mammalian cells are preferred. Cloning vehicles for use in mammalian cells will comprise a promoter capable of directing the transcription of a foreign gene introduced into a mammalian cell. Also contained in the expression vector is a polyadenylation signal, located downstream of the insertion site. The polyadenylation signal can be that of the cloned androgen receptor gene, or may be derived from a heterologous gene.

A selectable marker, such as a gene that confers a selectable phenotype, is generally introduced into the cells along with the gene of interest. Preferred selectable markers include genes that confer resistance to drugs, such as neomycin, hygromycin and methotrexate. Selectable markers may be introduced into the cell on a separate plasmid at the same time as the gene of interest, or they may be introduced on the same plasmid.

The copy marker of the integrated gene sequence can be increased through amplification by using certain selectable markers. Through selection, expression levels may be substantially increased.

Androgen receptor proteins may be purified from the host cells or cell media according to the present invention using techniques well known to those in the art. Such proteins may be utilized to produce monoclonal or polyclonal antibodies according to the techniques described below.

The techniques of this invention offer considerable advances over existing technology for measurement of androgen receptor. Utilizing proteins and peptices containing the disclosed sequences monoclonal or polyclonal antibodies can be produced for use as immunochemical reagents in immunodiagnostic assays. For example, radioimmunoassays and ELISA assays can be developed utilizing these reagents which will allow detection and quantification of androgen receptor in the presence of endogenous androgen since such androgen will not interfere with antibody binding to the receptor.

Immunocytochemistry utilizing our reagents enables determination and quantification of the cellular distribution of the androgen receptor in tumor tissues, which are often heterogenous in composition. This assay offers great potential for diagnostic evaluation of prostate cancer to determine to responsiveness to androgen withdrawal therapy.

In addition, the antibodies produced using the disclosed amino acid sequences can also be used in processes for the purification of androgen receptor protein produced by the above methods. One such purification process is disclosed in Logeat, F., et al., *Biochemistry* vol. 24 (1985), pp. 1029–1035, which is incorporated by reference herein.

Androgen receptor proteins and polypeptides synthesized from the deduced amino acid sequence can be used as immunogens for the preparation of antibodies to the androgen receptor. Peptides for such use range in length from about 3 to about 958 amino acids in length and are preferrably from about 15 to about 30 amino acids in length. Shorter peptides may have significant sequence homology to other steroid receptor proteins and larger peptides may contain multiple antigenic determinants; these properties could result in antibodies with cross-reactivities to other steroid receptor proteins.

Peptides can be synthesized from amino acid sequences in the $NH_2$-terminal region, the DNA-binding domain, and the carboxyl-terminal steroid binding domain. Peptide selection will be based on hydropathic plots, selecting hydrophilic regions that are more likely exposed on the receptor surface. For diagnostic purposes preferred sequences will be selected from the $NH_2$-terminal region where there is the least homology with other steroid receptor proteins.

Peptides for use as immunoyens can be syntnesized using techniques available to one of ordinary skill in the art. For example, peptides corresponding to androgen receptor sequences can be synthesized using tBOC chemistry on a Biosearch Model 9500 peptide synthesizer. Peptide purity is assessed by high pressure liquid chromatography. Peptides can be conjugated to keyhole limpet hemocyanin through cysteine residues using the coupling agent m-maleimidobenzoyl-N-hydroxysuccinimide ester. One can also prepare resin-bound peptides utilizing the p-(oxymethyl benzamide) handle to attach the C-terminal amino acid to solid-phase resin support.

Proteins and peptides of this invention can be utilized for the production of polyclonal or monoclonal antibodies. Methods for production of such antibodies are known to those of ordinary skill in the art and may be performed without undue experimentation. One method for the production of monoclonal antibodies is described in Kohler, G., et al., "Continuous Culture of Fused Cells Secreting Antibody of Predefined Specificity," *Nature*, vol. 256 (1975), p. 495, which Is incorporated herein by reference. Polyclonal antibodies, by way of example, can be produced by the method described below.

Peptide conjugates or resin-bound peptides can be injected into rabbits according to the procedure of Vaitukaitis et al., J Clin Endocrinol Metab, 33, 988–991 (1971) using a standard immunization schedule. Antisera titers can be determined in the ELISA assay.

For example, one androgen receptor sequence, $NH_2$Asp-His-Val-Leu-Pro-Ile-Asp-Tyr-Tyr-Phe-Pro-Pro-Gln-Lys-Thr (SEQ ID NO:26) in the 5' region upstream from the DNA-binding domain, was used to raise antisera in rabbits. The antisera react selectively at a dilution of 1 to 500 with the androgen receptor both in its untransformed 8–10S form and in its 4–5S transformed form. Receptor sedimentation on sucrose gradients increases from 4 to 8–10 S in the presence of antiserum at high ionic strength and from 8–10S to 11–12S at low ionic strength sucrose gradients. In the ELISA reaction against the peptide used as immunogen, reactivity was detectable at 1 to 25,000 dilution. This antiserum at a dilution of 1 to 3000 was found effective in staining nuclear androgen receptor in rat prostrate and other male accessory sex glands (data not shown).

Our invention provides new molecular probes comprising complementary DNA sequences derived from the deduced sequences encoding the androgen receptor for diagnostic purposes. Such probes may be used to detect the presence of androgen receptor mRNA In tumor cells. Such probes may also be used for detection of androgen receptor gene defects. Androgen receptor complementary DNA sequences can be used as hybridization probes to detect abnormalities in the androgen receptor gene or in its messenger RNA.

Androgen receptor DNA sequences disclosed and complementary RNA sequences can be used to construct probes for use in DNA hybridization assays. An example of one such hybridization assay and methods for constructing probes for such assays are disclosed in U.S. Pat. No. 4,683,195 to Mullis et al., U.S. Pat. No. 4,683,202 to Mullis, U.S. Pat. No. 4,617,261 to Sheldon, III et al., U.S. Pat. No. 4,683,194 to Salki et al., and U.S. Pat. No. 4,705,886 to Levenson et al., which are hereby incorporated by reference.

By example, one method for detecting gene deletion utilizes Southern blotting and hybridization. DNA can be isolated from cultured skin fibroblasts or from leukocytes obtained from blood. DNA is cut with restriction enzymes, electrophoresed on an agarose gel, blotted onto nitrocellulose, and hybridized with $[^{32}P]$-labeled androgen receptor DNA (see Maniatis, T. et al., Molecular Cloning, A Laboratory Manual, Cold Spring Harbor Laboratory, 1982, incorporated by reference herein).

In addition, small mutations can be detected utilizing methods known to one of ordinary skill in the art, from cultured skin fibroblasts of the affected individual. A cDNA library can be prepared using standard techniques. The androgen receptor clones can be isolated using a [$^{32}$P]DNA AR probe. The AR cDNA clones can then be sequenced and compared to normal AR cDNA sequences.

Alternatively genomic DNA can be isolated from blood leukocytes or cultured skin fibroblasts of the affected individual. The DNA is then subjected to restriction enzyme digestion, electrophoresis and is blotted onto nitrocellulose. Synthetic oligonucleotides can be used to bracket specific exons. Exon sequences are amplified using the polymerase chain reaction, cloned into M13 and sequenced. The sequences are compared to normal human AR DNA sequences.

Another method of identifying small mutations or deletions takes advantage of the ability of RNase A to cleave regions of single stranded RNA in RNA:DNA hybrids. Genomic DNA isolated from fibroblasts of affected individuals is hybridized with radioactive RNA probes (Promego Biotec) prepared from wild-type androgen receptor cDNA. Mismatches due to mutations would be cleaved by RNase A and result in altered sized bands relative to wild-type on denaturing polyacrylamide gels.

Restriction fragment length polymorphism (RFLP) linked to the androgen receptor gene locus may be used in prenatal diagnosis and carrier detection of androgen insensitivity. For example, the presence of RFLPs in normal individuals is first established by isolating DNA from lymphocytes of at least six females (total of 12 X chromosomes). DNA can be isolated using the proteinase K procedure and fragmented using a battery of restriction enzymes. Preferred are those enzymes that contain the dinucleotide sequence CG in their recognition sequence. Southern blots are screened with 5–10 kb androgen receptor genomic fragments which if possible lack repetitive DNA. For those regions containing repetitive elements, total human genomic DNA can be added as competitor in the hybridization reaction. Alternatively, one can subclone selected regions to yield a probe free of repetitive elements.

Figure 8:
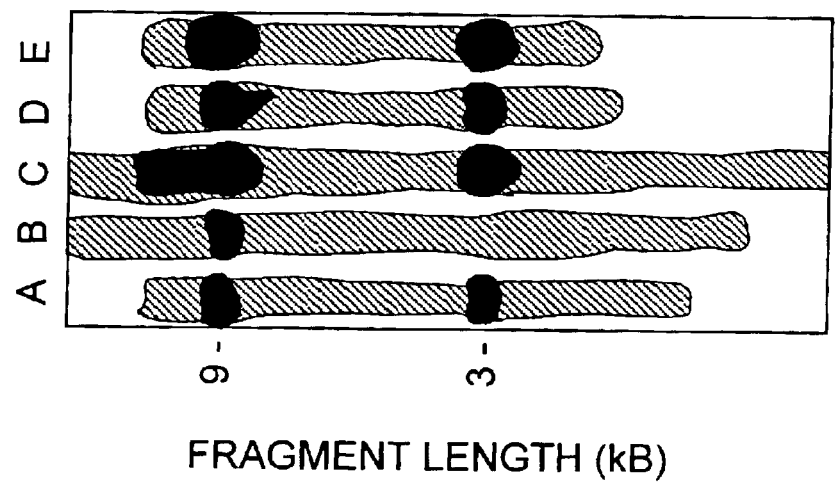
FIG. 8 is a photograph showing a Southern blot analysis in the human androgen receptor gene in complete androgen insensitivity syndrome patients.
Figure 7:
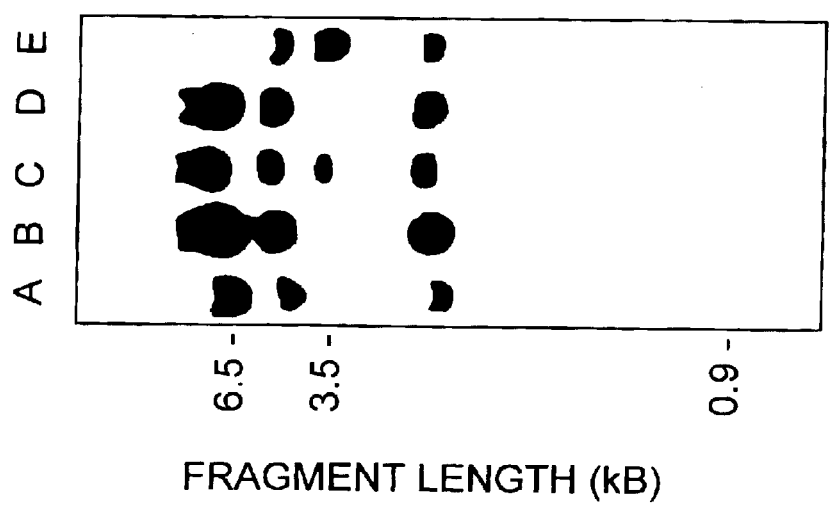
FIG. 7 is a photograph showing restriction fragment length polymorphisms in the human androgen receptor gene.

For example, a human restriction fragment length was determined by cDNA probe (B) and Hind III restriction endonuclease using the Southern blot technique (See FIG. 7). The two RFLP alleles detected are a fragment at 6.5 kb (allele 1) and a fragment at 3.5 kb (allele 2). Major constant fragment bands are seen at approximately 2 and 5 kb with minor constant bands at 0.9 and 7.5 kb. Allele 1 is present in approximately 30% of the X chromosomes of the Causasian population. Allele 2 is present in approximately 20% of the X chromosomes of the Causasian population. In FIG. 8 Lanes A, B and D, DNA from women who are homozygous for allele 1 is shown. In FIG. 8 Lane C, DNA from a woman who is heterozygous for both alleles 1 and 2 is shown. FIG. 8 Lane E contains DNA from a man that only possesses allele 2. This RFLP, and others determined by the clones we have isolated, will enable one to monitor the androgen receptor gene in various disease conditions described herein.

An example of using the androgen receptor clones to detect mutations is shown in FIG. 8 where five different complete androgen insensitive patients' DNA are digested with EcoRI, electrophoresed, Southern blotted, and probed with cDNA probe B. The patient in lane B lacks a 3 kb band indicating that part of the androgen receptor gene is deleted. Further analysis of this and other patients DNA is possible with other AR probes and by sequencing by standard methods and comparing the abnormal sequence to the normal sequence described herein.

Other potential uses for oligonucleotide sequences disclosed, for example in construction of therapeutics to block genetic expression, will be obvious to one of ordinary skill in the art.

What is claimed is:

1. An isolated and purified DNA sequence encoding a human androgen receptor comprising SEQ ID NO: 18.

2. An isolated and purified DNA sequence encoding a human androgen receptor selected from the group consisting of:
   a) the amino acid sequence SEQ M NO: 19;
   b) sequences which differ from (a) above due to the degeneracy of the genetic code and which encode a human androgen receptor encoded by (a) above.

3. An isolated and purified DNA sequence encoding a human androgen receptor selected from the group consisting of:
   a) the nucleotide sequence SEQ ID NO: 18;
   b) DNA sequences which differ from the DNA of (a) above due to the degeneracy of the genetic code and which encode a human androgen receptor encoded by (a) above.

4. A prokaryotic or eukaryotic host cell transformed or transfected with the DNA sequence of claim 2.

5. A viral or circular DNA plasmid comprising the DNA sequence of claim 2.

6. The viral or circular DNA plasmid according to claim 5 further comprising an expression control sequence operatively associated with said DNA sequence.

7. A prokaryotic or eukaryotic host cell transformed or transfected with the DNA sequence of claim 3.

8. A viral or circular DNA plasmid comprising the DNA sequence of claim 3.

9. The viral or circular DNA plasmid according to claim 8 further comprising an expression control sequence operatively associated with said DNA sequence.

* * * * *